United States Patent
Charrier et al.

(10) Patent No.: US 10,670,602 B2
(45) Date of Patent: Jun. 2, 2020

(54) METHOD FOR DETECTING A COLORECTAL LESION

(71) Applicants: bioMERIEUX, Marcy-l'Etoile (FR); Chu de Dijon, Dijon (FR)

(72) Inventors: Jean-Philippe Charrier, Tassin la Demi-Lune (FR); Genevieve Choquet-Kastylevsky, Francheville (FR); Tanguy Fortin, Lyons (FR); Hader Haidous, Saint Etienne (FR); Jerome Lemoine, Lucenay (FR); Arnaud Salvador, Villeurbanne (FR); Jean Faivre, Talant (FR)

(73) Assignees: BIOMERIEUX, Marcy L'Etoile (FR); CHU DE DIJON, Dijon (FR)

(*) Notice: Subject to any disclaimer, the term of this patent is extended or adjusted under 35 U.S.C. 154(b) by 116 days.

(21) Appl. No.: 14/765,432

(22) PCT Filed: Jan. 31, 2014

(86) PCT No.: PCT/FR2014/050177
§ 371 (c)(1),
(2) Date: Aug. 3, 2015

(87) PCT Pub. No.: WO2014/118475
PCT Pub. Date: Aug. 7, 2014

(65) Prior Publication Data
US 2015/0362494 A1  Dec. 17, 2015

(30) Foreign Application Priority Data

Feb. 1, 2013 (FR) .................................. 13 50908

(51) Int. Cl.
*G01N 33/574* (2006.01)
*H01J 49/42* (2006.01)

(52) U.S. Cl.
CPC .... *G01N 33/57419* (2013.01); *H01J 49/4225* (2013.01)

(58) Field of Classification Search
None
See application file for complete search history.

(56) References Cited

U.S. PATENT DOCUMENTS

2002/0160382 A1\* 10/2002 Lasek .................. C07K 14/47
                                                    435/6.14
2010/0151456 A1\*  6/2010 Ataman-Onal ............................
                                                    G01N 33/57419
                                                    435/6.14

FOREIGN PATENT DOCUMENTS

WO       0033083 A1   6/2000
WO    2009019368 A2   2/2009
WO    2010004214 A1   1/2010

OTHER PUBLICATIONS

ALPCO TM Immunoassays, L-FABP (Liver Fatty Acid Binding Protein) ELISA, pp. 1-11, Oct. 28, 2010.*

(Continued)

*Primary Examiner* — Alana Harris Dent
(74) *Attorney, Agent, or Firm* — Cantor Colburn LLP

(57) ABSTRACT

The invention relates to a method for detecting a colorectal lesion likely to evolve into invasive colorectal cancer, in a patient, by determining the presence of Liver Fatty Acid-Binding Protein (LFABP), in a biological sample of the patient, distant form the lesion.

9 Claims, 3 Drawing Sheets
Specification includes a Sequence Listing.

(56) References Cited

OTHER PUBLICATIONS

Abbatiello et al. Design, Implementation and Multi-Site Evaluation of a System Suitability Protocol for the Quantitative Assessment of Instrument Performance in LC-MRM-MS. Molecular and Cellular Proteomics. May 20, 2013.*

International Search Report for International Application No. PCT/FR2014/050177, International Filing Date Jan. 31, 2014, dated May 6, 2014, 3 pages.

Kohler et al.; "Continuous cultures of fused cells secreting antibody of predefined specificity"; Nature Publishing Group vol. 256; Aug. 7, 1975; p. 495-497.

Kohler et al.; "Derivation of specific antibody-producing tissue culture and tumor lines by cell fusion"; Eur. J. Immunol, vol. 6; 1976; pp. 511-519.

Lam et al.; "Identification of distinctive protein expression patterns in colorectal adenoma"; Proteomics Clinical Applications vol. 4, No. 1; Jan. 1, 2010; pp. 60-70.

Lauriola et al.; "Identification by a Digital Gene Expression Displayer (DGED) and test by RT-PCR analysis of new mRNA candidate markers for colorectal cancer in peripheral blood"; International Journal of Oncology, vol. 37; 2010; pp. 519-525.

Lawrie et al.; "Liver fatty acid binding protein expression in colorectal neoplasia"; British Journal of Cancer, vol. 90; 2004; pp. 1955-1960.

Lee et al.; "Differential expression in normal-adenoma-carcinoma sequence suggests complex molecular carcinogenesis in colon"; Oncology Reports, vol. 16; 2006; pp. 747-754.

Lyall et al.; "Profiling Markers of Prognosis in Colorectal Cancer"; Clinical Cancer Research, The American Association for Cancer Research, vol. 12, No. 4; Feb. 15, 2006; pp. 1184-1191.

Pei et al.; "Proteome Analysis and Tissue Microarray for Profiling Protein Markers Associated with Lymph Node Metastasis in Colorectal Cancer"; Journal of Proteome Research, vol. 6, No. 7; 2007; pp. 2495-2502

* cited by examiner

SEQUENCE LISTING

<160> NUMBER OF SEQ ID NOS: 7

<210> SEQ ID NO 1
<211> LENGTH: 56
<212> TYPE: PRT
<213> ORGANISM: Homo sapiens

<400> SEQUENCE: 1

Met Ser Phe Ser Gly Lys Tyr Gln Leu Gln Ser Gln Gln Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser
    50                  55

<210> SEQ ID NO 2
<211> LENGTH: 65
<212> TYPE: PRT
<213> ORGANISM: Homo sapiens

<400> SEQUENCE: 2

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val
65

<210> SEQ ID NO 3
<211> LENGTH: 12
<212> TYPE: PRT
<213> ORGANISM: Homo sapiens

<400> SEQUENCE: 3

His Leu Ser Glu Tyr His Pro Trp His Pro Arg Ala
1               5                   10

<210> SEQ ID NO 4
<211> LENGTH: 26
<212> TYPE: PRT
<213> ORGANISM: Homo sapiens

<400> SEQUENCE: 4

```
Thr Glu Leu Asn Gly Asp Ile Ile Thr Asn Thr Met Thr Leu Gly Asp
1               5                   10                  15

Ile Val Phe Lys Arg Ile Ser Lys Arg Ile
            20                  25

<210> SEQ ID NO 5
<211> LENGTH: 11
<212> TYPE: PRT
<213> ORGANISM: Homo sapiens

<400> SEQUENCE: 5

Ala Ile Gly Leu Pro Glu Glu Leu Ile Gln Lys
1               5                   10

<210> SEQ ID NO 6
<211> LENGTH: 10
<212> TYPE: PRT
<213> ORGANISM: Homo sapiens

<400> SEQUENCE: 6

Gly Val Ser Glu Ile Val Gln Asn Gly Lys
1               5                   10

<210> SEQ ID NO 7
<211> LENGTH: 10
<212> TYPE: PRT
<213> ORGANISM: Homo sapiens

<400> SEQUENCE: 7

Thr Val Val Gln Leu Glu Gly Asp Asn Lys
1               5                   10
```

METHOD FOR DETECTING A COLORECTAL LESION

TECHNICAL FIELD

The invention relates to the detection of colorectal lesions in non-cancerous stage but which are likely to evolve into invasive colorectal cancer, and to the detection of tumors in situ (Tis, also called carcinoma in situ or intra-mucous, of stage T0), also likely to degenerate into invasive cancers.

BACKGROUND

Due to their similarities, colon and rectum cancers are generally grouped under the term of colorectal cancer (CRC). Colorectal cancer tumors grow at the expense of the mucosa of the colon (or colonic), most often in the sigmoid, which is located in the last part of the colon, with regard to colon cancers, and below this area, with regard to rectum cancers. The most common form of these cancers is called adenocarcinoma.

The normal colonic mucosa is composed of a glandular epithelium monostratified, polarized, continuous, organized in the form of crypts, limited by a basement membrane, and surrounded by lamina propria. Crypts are disposed perpendicularly to the muscularis mucosa. Lamina propria, also called chorion, has cellular (inflammatory and mesenchymal cells), stromal and vascular contents, variable according to the location in the colon. Its limitation in depth is composed by the muscularis mucosa. In lamina propria, the vascularization is limited to endothelial venules and capillaries, and to lymphatic channels superficially to the muscularis mucosa.

There are different types of benign tumors, that is to say non-cancerous colorectal tumors. The macroscopic term of polyp refers to any sessile or pedunculated mass protruding in the colonic lumen, whatever its histological nature. Histologically, adenomas are likely to turn into cancer. Hyperplastic polyps are not precancerous lesions. The same applies for inflammatory pseudo-polyps or juvenile polyps. Colonic carcinogenesis is relatively well known. In the West, colorectal cancer grows in 60-85% of cases from adenoma. This can be pedunculated, sessile or even barely in relief in the case of flat adenoma. Adenoma is a circumscribed focus of epithelial dysplasia. It is generally admitted that on 1000 adenomas, 100 will reach the size of 1 cm and 25 will evolve into cancer within 10 to 20 years. The cumulative probability of cancerous transformation of adenoma with diameter greater than or equal to 1 cm was calculated. It is of 2.5% at 5 years, 8% at 10 years and 24% at 20 years. The risk of carcinomatous transformation increases with the number, the size of adenoma (>=1 cm), the presence of villous contingent and the existence of a severe dysplasia. Adenomas presenting at least one of these criteria constitute adenomas with high risk for colonic transformation.

The adenoma-carcinoma sequence is now well established:
The prevalence of adenomas with high-risk of malignant transformation and invasive colorectal carcinomas is high in the same populations;
The peak of incidence of adenomatous polyps precedes by a few years that of cancer;
The risk of cancer depends on the number of adenomas, which explains the inevitable characters of transformation of familial polyposis that are characterized by the presence of more than 200 adenomas;
On parts of colectomy, adenoma lesions are frequently observed to the contact with infiltrating carcinomatous focus;
The incidence of colorectal cancer is decreased after exeresis of adenomas.

The degree of dysplasia adenomas is assessed according to the differentiation, cytology and architecture abnormalities. All adenomas are dysplastic, but low-grade (formerly mild or moderate) and high-grade (severe) dysplasia are distinguished. Any benign adenoma is by definition in a low grade dysplasia, but may subsequently evolve into high-grade dysplasia adenoma, generally associated with its increase in size greater than 1 cm diameter.

In practice, adenoma-cancer sequence progresses from low grade dysplasia adenoma to invasive carcinoma, with the different steps below:
Low-grade dysplasia
High-grade Dysplasia
Tumor in situ (Tis, or intra epithelial or intra mucosal carcinoma)
Invasive carcinoma from the invasion of the submucosa.

In a general manner, cancer in situ is a cancer in its initial stage of development, remaining limited to the tissue that gave it birth. Its definition is microscopic. In invasive carcinomas of colon, malignant cells crossed the muscularis mucosa and reached at least the submucosa (stage T1 of the TNM classification) or the muscularis mucosa (stage T2). The muscularis mucosa is a thin layer of smooth muscles, crossed by lymphoglandular complexes, vascular channels and nerve cells.

As we progress from stage T0 to stage T4, there is at tissue level a more and more significant architectural disorganization. The extension is made toward the serosa, often with a lymphatic invasion. The infiltration of cancer may be associated with vascular invasion or perinervous sheathing by tumor cells. Carcinoma may be more or less well differentiated, whatever its stage.

It is the basement membrane degradation then the crossing of the muscularis mucosa that will allow tumor cells migration and cancer spread. Invasive colorectal carcinomas are classified following the International Classification TNM as stage I to IV cancer.

Tumors in situ T0 (Tis, or intra-epithelial or intra-mucosal carcinoma) may be considered as corresponding to stage 0 which does not exist in the TNM classification, because they are not considered as cancer, since they are not invasive and not likely to be accompanied neither by a ganglionic invasion nor by metastases. However, they are lesions likely to evolve into invasive cancer and should therefore be detected to perform the exeresis and prevent the evolution into an invasive cancer.

In practice, the secretion of tumor markers is generally proportional to the tumor stage. Architectural disorganization, tissue invasion, and the presence of vascular emboli promote the release of tumor markers in biological fluids, as they promote the dissemination of cancer at a distance by the migration of tumor cells. When the basement membrane is not crossed, as is the case in the adenomas and in the noninvasive intraepithelial carcinomas, or when cancer is strictly intramucosal, the release of markers in the circulation is unlikely to happen, which is not the case when the tumor is invasive and especially when there are vascular or nervous emboli. Unexpectedly, the Applicant discovered that the protein Liver-Fatty Acid-Binding Protein (LFABP) constitutes a marker, remotely, of non-cancerous colorectal lesions and of tumors in situ. The detection of such lesions of which evolution into invasive carcinoma is significantly high, allows their exeresis, and thus to reduce the number of invasive colorectal cancer and the mortality due to this cancer.

This protein, LFABP (Swiss Prot No. P07148, also called L_FABP, FABP1, FABPL, protein Z or sterol transporter protein) belongs to the FABP family which comprises nine isoforms. Each isoform is named according to the tissue in which it was detected for the first time. These isoforms possess a community of functions, similar three-dimensional structures but their sequence homology is not high. The LFABP has been sequenced in 1985. It is a small protein of 15 kDa, abundant in the cytosol and having the ability to bind to free fatty acids and also to bilirubin.

For colon cancer, several groups identified a decrease in the expression of LFABP protein in the tumor tissue (neoplastic or pre-neoplastic) compared to normal colonic mucosa, by using 2 dimensions electrophoresis techniques. This result was also confirmed by immunohistochemistry techniques. Tissue expression of LFABP is decreased in primary colorectal tumor in patients with ganglionic nodes compared to patients without ganglionic nodes.

Furthermore, the expression of mRNA of LFABP and the protein itself are decreased during the sequence "normal tissue/adenoma/colorectal cancer", as it has been demonstrated by many authors [Lee et al., *Differential expression in normal-adenoma-carcinoma sequence suggests complex molecular carcinogenesis in colon. Oncol Rep.* 2006 October; 16(4):747-54], which means that LFABP should be fewer in adenomas tissue than in normal tissue. Lauriola et al. [Lauriola M et al., *Identification by a Digital Gene Expression Displayer (DGED) and test by RT-PCR analysis of new mRNA candidate markers for colorectal cancer in peripheral blood. Int J Oncol.* 2010 August; 37(2):519-25] tried to quantify mRNA circulating in blood for the LFABP and other markers, without managing to detect LFABP neither in cancer patients nor in control subjects.

In patent application WO2009/019368A2, the Applicant highlighted the fact that the detection of LFABP protein, in combination with CEA markers (carcinoembryonic antigen) and CA 19-9, allowed improving the detection of colorectal cancer patients.

BRIEF SUMMARY

The Applicant now surprisingly discovered that LFABP is released by non-cancerous colonic lesions, that is to say, adenomas and noninvasive lesions Tis T0, and this is in abundant way, which was not predictable since in noninvasive colonic lesions, the basement membrane is not crossed, making more than improbable the release of markers in the circulation. FABP may thus be detected in biological samples distant from tumors.

Thereby, the disclosure concerns a method for detecting a colorectal lesion likely to evolve into invasive colorectal carcinoma (or cancer), in a patient, by determining the presence of Liver Fatty Acid-Binding Protein (LFABP). According to a variant of the method of the invention, such colorectal lesion is detected, in vitro, in biological sample of the patient.

The invention also relates to a method of screening, in vitro, of a colorectal lesion in a population by determining the presence of LFABP in a biological sample of an individual.

A method of the invention may further comprise a highlight of a variation in the expression of LFABP. Advantageously, an increase in the expression of LFABP is highlighted. This variation may be observed by comparison to a reference population called control, of non-suspected CRC patients, for example patients that had a coloscopy which proved to be normal, or by comparison to a predetermined reference value. Preferably, the variation is observed with respect to a reference population, for samples of the same nature.

The invention also relates to applications of a method of the invention. It relates notably to a method for detecting a sensitivity to colorectal cancer, in a patient, which implements a method of the invention. According to a variant, this sensitivity is carried out in vitro, by a detection in a biological sample.

According to the invention, it is meant by colorectal lesion likely to evolve into invasive colorectal cancer or carcinoma, a non-cancerous lesion, such as an adenoma, dysplastic adenoma with low grade or high-grade dysplasia, carcinoma in situ (intra epithelial or intra mucosal), as defined previously. Indeed, as explained above, a carcinoma in situ is not invasive, it is at the stage 0 (T0), but due to its histology, its probability to evolve into invasive cancer is greater than that of dysplastic adenoma.

According to the invention, it is meant by release by colonic tumors, the active or passive secretion or the release, whatever the mechanism, of the tumor marker, by colorectal lesions.

Compared to other known tumor markers as carcinoembryonic antigen or CA 19-9, the detection of LFABP allows preventing invasive colorectal cancer (CRC).

Relative to the prior art, this marker not only prevents a CRC, in the absence of any suspicion of invasive CRC in the patient, but it may be detected in any biological sample, and very advantageously in any sample distant from the lesion.

It is meant by biological sample, any sample likely to contain LFABP and/or at least one representative tracer of LFABP. This sample may come from a sample of any biological fluid, as whole blood, serum, plasma, urine, cerebrospinal fluid, organic secretions, saliva, effusions, feces, bone marrow, and cells purified from these liquid samples, or from a tissue sample or a tissue, or isolated cells. Preferably, the sample is distant from the potential lesion.

By determining the presence or the expression of LFABP, it is understood that LFABP and/or at least one representative tracer of LFABP is detected. This tracer is characteristic of the presence of LFABP. According to the content of LFABP in the patient or in the biological sample and according to the technique used, the detection of a cited tracer may be more relevant than that of the LFABP on itself. Therefore, a tracer may be chosen among precursors of LFABP, metabolites of LFABP and any molecule associated with the biological activity of LFABP, in particular the enzymatic activity of LFABP, products of degradation or of cleavage of the LFABP, or an immune response due to LFABP. Therefore, a tracer of LFABP is preferably chosen among peptides, preferably peptides mixtures of LFABP; nucleic acids, preferably messenger RNAs; a modification of the gene encoding for the LFABP, as its promoter's methylation, or a modification of the nucleic acid leading to a modification of the expression of LFABP; antibodies recognizing specifically the LFABP and produced in the patient in response to a presence of LFABP, by immunogenic reaction.

A preferred tracer is an antibody chosen among those recognizing specifically a sequence of peptide chosen among SEQ ID NO: 1, SEQ ID NO: 2, SEQ ID NO: 3 and SEQ ID NO: 4.

Other advantageous tracers are selected among peptides presenting the following sequence SEQ ID NO: 1, SEQ ID NO: 2, SEQ ID NO: 3, SEQ ID NO: 4, SEQ ID NO: 5, SEQ ID NO: 6 and SEQ ID NO: 7, and their mixtures.

More particularly, according to a method for detecting a colorectal lesion, LFABP and/or at least one representative tracer of LFABP is detected and/or at least one biological activity, for example enzymatic, specific to LFABP is measured in said biological sample.

Different methods may be implemented by any appropriate technique well known by the one skilled in the art.

Therefore, LFABP may be assayed by mass spectrometry quantitative technique, by any immunological technique, or a combination of both techniques, or by any enzymatic technique. For example, LC-MRM-MS technique which combines liquid chromatography and mass spectrometry in the MRM (Mutiple Reaction Monitoring) mode, may be used.

The method of the invention may be improved by detecting, besides to LFABP, at least another marker allowing the detection of colorectal lesion at non-cancerous stage, when appropriate also released by colonic lesions outside the tissues. Therefore, the combination of at least two markers allows improving the specificity and the sensitivity of the diagnostic test of the lesions likely to evolve into invasive CRC.

BRIEF DESCRIPTION OF THE DRAWINGS

Different variants of the method are exposed in the following examples, with reference to FIGS. 1-5 according to which:

FIGS. 3, 4 and 5 represent the results of ELISA assay on Vidas®, of LFABP, CEA marker and CA19-9 marker, respectively, in patients at different stages of tumors, stage Tis and invasive CRC from TNM stage I to IV, as described in example 4.

DETAILED DESCRIPTION AND EXAMPLES

EXAMPLE 1

Obtaining Monoclonal Antibodies Directed Against LFABP

1) Obtaining the Recombinant Protein

Figure 1:
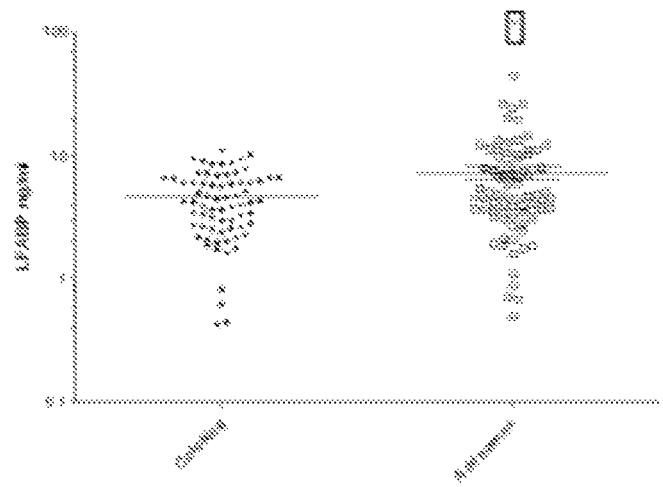
FIG. 1 represents the results of ELISA assay of LFABP on Vidas®, in control patients presenting a negative coloscopy (ColoNeg) and patients presenting adenomas, as described in example 3.

To carry out immunizations and obtain monoclonal antibodies against LFABP protein, the LFABP recombinant protein was first obtained.

The complementary DNA, the expression vectors, the cloning and the obtaining of the LFABP recombinant protein (expression and purification) were carried out in the same way as described in patent WO2010/004214.

2) Immunizations 2.1) Animal Model

The immunization experiments were carried out in 6 to 8 weeks old BALB/c (H-$2^d$) female mice at the time of first immunization.

2.2) Immunogenes and Immunizations

In order to increase the immune responses obtained in mice and to generate monoclonal antibodies, LFABP protein was produced in the form of recombinant protein produced according to the operating modes described in patent WO2010/004214A1. The protein was mixed volume per volume with Freund's adjuvant (Sigma), prepared in the form of water-in-oil emulsion, and which is known to present a good immunogenic power. Three mice were immunized. The mice received three successive assays of 10 µg of immunogen at 0, 2 and 4 weeks. All injections were carried out subcutaneously. The first injection was made as a mixture with complete Freund's adjuvant, the two following injections were made in mixture with incomplete Freund's adjuvant. Between Days 50 and 70 after the first injection, humoral responses were restimulated with an intravenous injection of 100 µg of recombinant protein.

2.3) Follow-up of the Apparition of Humoral Response

In order to follow up the apparition of antibodies, blood samples from mice are collected regularly. The presence of anti-tumor marker antibodies is tested by using an ELISA. The protein of interest is used for capture (1 µg/well), after saturation the antigen is reacted with different dilutions of the serums to be tested (incubation at 37° C. for 1 h). Specific antibodies present in the serum are revealed with AffiniPure goat anti-mouse IgG antibody conjugated to alkaline phosphatase (H+L, Jackson ImmunoResearch, Cat no. 115-055-146), which binds to the sought antibodies (0.1 µg/well).

2.4) Obtaining Monoclonal Antibodies

Three days after the last injection, for each tumor marker, one of the immunized mice was sacrificed; blood and spleen were collected. The splenocytes obtained from the spleen were cultured with myeloma cells Sp2/0-Ag14 so that they merge and immortalize, according to the protocol described by Köhler et Milstein [G. Köhler et C. Milstein, 1975, Nature, 256, 495-497; G. Köhler et C. Milstein, 1976, Eur J Immunol, 6, 511-519].

After a period of incubation of 12-14 days, the supernatants of hybridomas obtained were screened to determine the presence of anti-tumor marker antibodies by using ELISA test described in point 3 of this example. Positive hybridoma colonies were sub-cloned twice according to the limiting dilution technique, well known by the one skilled in the art.

3) Monoclonal Antibodies Characterization

The list of monoclonal antibodies obtained is shown in Table 1. These monoclonal antibodies were analyzed by the Western blot technique.

TABLE 1

| Monoclonal antibodies |
| --- |
| 2E5G9 |
| 3A7B4 |
| 5A8H2 |
| 2C9G6 |
| 3D6G1 |
| 8B10B8 |
| 7D8A11 |

3.1) Antibodies Complementarity

In order to be able to construct ELISA test allowing to assay the samples of patients, the complementary of the antibodies is first tested. These are the same antibodies which are used in capture or revelation (after biotinylation). Each antibody of biotinylated revelation is tested with each capture antibody (VIDAS® cone antibody). Couples are tested with the LFABP recombinant protein described above. Table 2 summarizes the results obtained for the different antibodies couples.

TABLE 2

Cross table showing the results obtained for each couple of antibodies with LFABP recombinant protein (signal average - background noise average in RFV). (RFV or Relative Fluorescence Value is the signal read by Vidas ®®).

| Capture | Detection | | | | | | |
|---|---|---|---|---|---|---|---|
|  | 2E5G9 | 3A7B4 | 5A8H2 | 2C9G6 | 3D6G1 | 8B10B8 | 7D8A11 |
| 2E5G9 | 10.5 | 16.5 | 25 | 10537 | 10377.5 | 5066 | 0.5 |
| 3A7B4 | 42 | 198 | 707.5 | 10071 | 9923 | 10009 | 24.5 |
| 5A8H2 | 36 | 109 | 513 | 10404 | 10283.5 | 9930 | 18.5 |
| 2C9G6 | 10753.5 | 10815 | 10708.5 | 1417.5 | 213 | 10774.5 | 1562 |
| 3D6G1 | 10136.5 | 10707.5 | 10684.5 | 606.5 | 138 | 10462 | 1038.5 |
| 8B10B8 | 8846 | 9940.5 | 9677 | 10385.5 | 10637.5 | 87 | 363.5 |
| 7D8A11 | 5.5 | 21.5 | 14 | 8053.5 | 8094.5 | 128 | 4.5 |

In the issue of these tests, the 6 following couples of complementary antibodies are retained:

3A7B4/3D6G1
5A8H2/3D6G1
2C9G6/5A8H2
3D6G1/5A8H2
8B10B8/5A8H2
2C9G6/2E5G9

3.2) Epitopes Characterization

Epitopes recognized by monoclonal antibodies were characterized by using Spotscan techniques, the screening of peptides banks carried by the phages, and the construction of chimeric proteins (fragments library).

3.2.1) Methodology

Spotscan technique, adapted according to Frank and Döring, allows to synthesize simultaneously a large number of peptides bound to a cellulose membrane. These peptides reproduce the sequence of the target antigen as peptides of 8 to 12 amino acids, overlapping from 1 to 4 residues. These peptides are then brought into contact with the antibody to be studied in a Blot type colorimetric test, and the identification of immunoreactive peptides allows to deduce the minimum sequence of the epitope of the antibody and to locate it specifically on the antigen.

The synthesis is performed on a cellulose membrane uniformly carrying arms made of polyethylene glycol (PEG) of a length ranging between 8 to 10 units, presenting a free $NH_2$ function at the end-of-chain. It takes place in the C-terminal end towards the N-terminal end of peptides. The amine function of the amino acids are protected by a Fmoc group (9-fluoremethyloxycarbonyl), and their side chains, likely to react during the synthesis, are also protected by trityl, t-butyl or t-butyl-ether groups. Stock solutions of amino acids are prepared at a concentration of 0.33 M in NMP (N-methyl-pyrrolidone) containing 0.5 M HOBt (hydroxybenzotriazole). The deposit of amino acids is performed using the ASP 222 robot (Abimed, Langenfeld, Germany), driven by AutoSpot XL software. The use of this robot allows making simultaneously up to 4 membranes of 96 spots, namely 384 peptides.

For a coupling cycle of an amino acid, the robot deposits 0.7 µl of the solution of amino acid activated extemporaneously (one volume of 1.1 M diisopropyl-carbodiimide solution diluted in NMP per 3 volumes of amino acid stock solution) on the membranes. This deposit is repeated a second time, then the membranes are rinsed in DMF (N,N-dimethylformamide). The $NH_2$ groups that have not reacted are then acetylated by 4 to 6 incubations of 10 minutes in 10% acetic anhydride solution in DMF, in order to avoid the apparition of abortive or truncated peptides. After 3 washes of 2 minutes in DMF, the Fmoc groups protecting the amine function of the amino acids are cleaved by incubation for 5 minutes in a 20% piperidine solution in DMF. After 4 washes in DMF, the spots are colcored with 1% bromophenol blue solution in DMF, then the membrane is rinsed 3 times with methanol and dried in the open air before the next coupling cycle.

This protocol is repeated for the addition of each new amino acid. After the last amino acid coupling, the peptides are acetylated in order to allow the blocking of all free $NH_2$ groups, thereby preventing the addition of another amino acid. Then the side chains of all peptides are deprotected by the incubation of the membranes in a trifluoroacetic acid/dichloromethane/triisobutylsilane (5:5:0.3) bath for 1 hour. The membranes are then rinsed 4 times in dichloromethane, 3 times in DMF and 3 times in methanol before being dried in the open air and kept at −20° C. until immunorevelation.

To immune-reveal spots with a monoclonal antibody, the membranes are first rinsed in methanol, then washed in TBS (Tris-HCl 50 mM pH 8.0, NaCl 140 mM, KCl 3 mM) before their incubation overnight at room temperature in the saturation solution (10× concentrated solution based on casein (Western Blocking Reagent, Roche) diluted in TBS-Tween 20 0.05% (TBS-T) and containing 5% sucrose). After a wash of 10 minutes in TBS-T, membranes are incubated for 1 h30 at 37° C. with monoclonal antibody diluted at 20 µg/ml in saturation solution. The membranes are then washed 3 times in TBS-T then incubated with anti-mouse conjugate coupled with alkaline phosphatase (Jackson lmmunoresearch), diluted at the $\frac{1}{2000}^{th}$ in the saturation solution. After 2 washes of 10 minutes in TBS-T, then 2 washes in CBS (10 mM acid citric acid pH 7, 140 mM NaCl, 3 mM KCl), the developer, extemporaneously prepared (5-bromo, 4-chloro, 3-indoyl, 600 µM Phosphate, 720 µM thiazolyl blue tetrazolium bromide, and 5 mM $MgCl_2$ in CBS), is brought into contact with the membrane for 30 to 45 minutes in the dark. Immunoreactive peptides appear in blue-violet. After 3 washes in distilled water, the membranes are scanned and kept in water until regeneration.

Regeneration allows to eliminate the antibodies and conjugates bound to peptides, which thereby allows to carry out a new immunoreactivity test vis-a-vis another antibody. The membranes undergo a series of washes of 10 minutes each: 1 wash in distilled water, 6 washes in DMF, 3 washes in regeneration buffer A (8 M urea, 35 mM SDS (sodium dodecyl sulfate), 0.1% β-mercaptoethanol), 3 washes in regeneration buffer B (distilled water/ethanol/acetic acid 4:5:1), then 2 washes in methanol. The membranes are then dried in the open air before their storage at −20° C.

The characterization of epitopes by screening of peptide banks carried by phages was carried out by using the commercial kit PhD12 Phage Display Peptide Library Kit (Cat. No. E#8110S) from New England Biolabs, by following the instructions supplied with the kit, Version 2.7 of the protocol dated November 2007.

A third technology of epitope location has been used: the construction of a fragments library of LFABP recombinant protein, against which the affinity of the antibodies of interest was tested.

3.2.2) Results

Table 3 summarizes the epitopes recognized by 5 LFABP antibodies whose epitopes were analyzed by the three mentioned techniques.

TABLE 3

| Antibodies | epitope N° | Epitope sequence[a] | Epitope type | Technique |
|---|---|---|---|---|
| 2C9G6 | 1 | N-term 1-56 (SEQ ID NO: 1) | Conformational | Fragments library |
| 3D6G1 | 1 | N-term 1-56 (SEQ ID NO: 1) | Conformational | Fragments library |
| 8B10B8 | 1 | N-term 1-56 (SEQ ID NO: 1) | Conformational | Fragments library |
| 5A8H2 | 2 | N-term 1-65 (SEQ ID NO: 2) (AA 57 to 65 necessary) | sequence Necessary for the binding | Fragments library |
|  | 3 | HLSEYHPWHPRA (SEQ ID NO: 3) | Conformationnel epitope Mimotope | Phage bank screening |
| 7D8A11 | 4 | 102-127 SEQ ID NO: 4 | Linear-epitope | Spotscan and fragments library |

[a]Amino acid sequence of the region binding the LFABP to the tested antibody. The numbers in parentheses correspond to the epitope position on the LFABP amino acid sequence, the numbering begining in the initial methionine.

Epitopes recognized by the antibodies 3A7B4 and 5A8H2 could not be determined by Spotscan technique, which indicates that they are not linear. Screening of peptides banks carried by the phages allowed to selec 1 mimotope (linear sequence mimicking an epitope) which reacts with the 5A8H2 antibody. Consensus sequence of this mimotope was aligned in order to determine a consensus sequence (SEQ ID NO: 3) which is indicated in Table 3, which represents the minimal sequence recognized by the antibody. It was not possible to find this consensus sequence in the primary structure (or peptide sequence) of LFABP. Therefore, this consensus sequence corresponds to residues situated in different locations on the primary structure of the protein but which share a similarity in its three-dimensional structure to form a conformational epitope. Furthermore, the use of recombinant protein fragments library allowed to localize the epitope for 2C9G6, 3D6G1 and 8B10B8 antibodies in the first 56 amino acids of the protein (SEQ ID NO: 1). The 5A8H2T antibody needs, for its part, 9 additional amino acids (AA 1 to 65) to be bound, binding site opposite the binding site of the 7D8A11 antibody (SEQ ID NO: 2). The 7D8A11 antibody is the only one having a linear epitope characterized by Spotscan (SEQ ID NO: 4).

The antibodies mentioned in Table 3 above are important to the invention. Compared to other known antibodies of LFABP, they constitute a more sensitive LFABP dosing tool.

EXAMPLE 2

Development of Sandwich ELISA Tests Against LFABP Protein on Vidas® Automaton

LFABP protein was assayed by means of the antibodies described in example 1 and of sandwich immunoassay type by using for example Vidas® ELISA automaton (bioMérieux). This type of test may also be carried out in microplate, in automated or manual way. As a first step, the different available antibodies were tested to choose a couple of functional antibodies, that is to say, at least one antibody able to capture the biomarker protein (capture antibody) and at least one antibody able to reveal the biomarker molecule (revelation antibody).

To this end, ELISA test was constructed by using the reagents of Vidas® HBs Ag Ultra kit (bioMérieux, Cat. No. 30315).

The reagents were used as described in the corresponding note (ref 11728D-FR-2005/05.), with the following modifications:

The cones were sensitized with one of the 5 Ac of capture selected and used at a concentration of 10 µg/ml.

The content of the second well of HBs Ag Ultra cartridge was replaced by 300 µl of revelation antibody, coupled with biotin, diluted to 1 µg/ml in the buffer of the second well of the Vidas®HBs Ag Ultra kit (buffer with goat serum and sodium azide at 1 g/l).

The serum sample (50 µl) was diluted directly in the second well of HBs Ag Ultra cartridge.

ELISA reaction was carried out by means of Vidas® automaton and HBS protocol whose step of incubation of the sample with the capture and revelation antibodies had been brought to 100 cycles.

The results were obtained in form of crude values after subtraction of the background noise (reading of the substrate before reaction).

A standard curve was established by dosing a range of concentrations of the recombinant biomarker protein. The standard curve was plotted by reporting on the abscissa the concentration of the biomarker protein, and on the ordinate the signal read by Vidas® (RFV or Relative Fluorescence Value). The concentration of the biomarker protein present in the body fluid to be assayed (blood, serum, plasma, feces) was calculated by plotting the concentration corresponding to the RFV signal read by Vidas®.

Equivalence of Various Developed ELISA Tests

We wanted to evaluate the correlation between the different developed sandwich immunoassays. Tests Vidas® were compared with each other and also compared to test commercialized by Hycult Biotechnology Company to assay the human LFABP protein (Cat. No. HK404), as described in patent application WO2009019368A2.

These equivalence tests were carried out through serum samples of patients suffering from colorectal cancer (CRC) or healthy blood donor control subjects (EFS), obtained respectively from hospital services within the framework of 2 Huriet law protocols, and from a french blood bank establishment (healthy subjects).

TABLE 4

LFABP assays in ng/ml obtained with the Hycult biotechnology commercial test and with the different developed Vidas ® tests

| Patient | Hycult | 2C9G6/ 5A8H2 | 5A8H2/ 3D6G1 | 2C9G6/ 2E5G9 | 3A7B4/ 3D6G1 | 3D6G1/5A8H2 | 8B10B8/ 5A8H2 |
|---|---|---|---|---|---|---|---|
| CBSE004 | 7.78 | | 2.87 | 1.74 | 2.57 | | |
| CBSE011 | 7.73 | | 1.92 | 1.33 | 1.72 | | |
| CBSE012 | 0.11 | | 2.31 | 1.83 | 2.07 | | |
| CBSE018 | | | 1.35 | 0.75 | 1.19 | | |
| CBSE019 | 6.65 | | 4.48 | 3.41 | 3.98 | | |
| CBSE023 | 8.21 | | 4.6 | 4.92 | 4.07 | | |
| CBSE025 | 16.38 | | 7.88 | 7.45 | 6.87 | | |
| CLSP043 | 2.89 | 1.94 | 2.49 | 1.7 | 2.47 | 2.29 | 0.22 |
| CLSP047 | 1.94 | | 1.39 | 0 | 1.22 | | |
| CLSP078 | 2.56 | | 13.01 | 8.27 | 11.33 | | |
| CLSP090 | 3.77 | | 1.18 | 0.98 | 1.04 | | |
| CLSP164 | 6.54 | 4.18 | 4.77 | 4.6 | 4.49 | 4.14 | 1.54 |
| CLSP165 | 7.86 | 1.27 | 1.68 | 1.8 | 2.32 | 1.82 | 1.64 |
| CLSP167 | 8.17 | 0 | 0.43 | 0 | 2.01 | 0 | 0.52 |
| CLSP170 | 6.02 | 4.36 | 4.26 | 4.61 | 4.16 | 3.6 | 2.11 |
| CLSP174 | 23.64 | 5.57 | 6.73 | 6.26 | 7.8 | 4.67 | 7.39 |
| CLSP182 | 7.25 | 4.47 | 4.61 | 5.5 | 4.46 | 4.21 | 4.06 |
| CLSP183 | 16.9 | 11.07 | 10.12 | 9.79 | 9.32 | 7.08 | 15.94 |
| CLSP185 | 19.63 | 5.35 | 7.01 | 6.36 | 8.41 | 4.44 | 5.32 |
| CLSP186 | 7.06 | 4.59 | 4.42 | 5.35 | 4.44 | 3.39 | 2.72 |
| CLSP189 | 5.34 | 0 | 0.25 | 0 | 1.16 | 0 | 0.69 |
| CLSP194 | 13.09 | 5.38 | 5.65 | 6.71 | 5.4 | 5.17 | 5.52 |
| CLSP198 | 8.16 | 2.2 | 3.1 | 3.14 | 4.24 | 2.88 | 1.94 |
| CLSP207 | 6.02 | 4.6 | 4.71 | 5.58 | 4.67 | 4.01 | 1.91 |
| GHBD020 | 2.24 | | 5.46 | 3.08 | 4.81 | | |
| GHBD021 | 1.84 | | 1.58 | | 1.41 | | |
| GHBD029 | 2.75 | | 3.42 | 2.74 | 3.05 | | |
| N000533 | 3.46 | 0.59 | 1.18 | 0.96 | 1.51 | 1.21 | 1.85 |
| N002301 | 7.78 | | 5.54 | 5.19 | 4.88 | | |
| N005702 | 2.74 | | 1.04 | 0.79 | 0.91 | | |
| N009944 | 3.49 | 1.41 | 2.06 | 2.66 | 1.9 | 1.98 | 1.69 |
| N011147 | 2.86 | 0.92 | 1.52 | 1.82 | 1.41 | 1.5 | 1.16 |
| N011968 | 2.06 | 1.26 | 1.56 | 1.64 | 1.62 | 1.65 | 0.97 |
| N011984 | 5.29 | 0.87 | 1.32 | 1.21 | 1.8 | 1.45 | 1.19 |
| N014106 | 2.66 | 0.45 | 0.91 | 0.66 | 1.25 | 0.89 | 0.74 |
| N015402 | 4.41 | | 1.34 | 0.9 | 1.18 | | |
| N017234 | 4.04 | 1.9 | 2.49 | 3.33 | 2.41 | 2.61 | 2.48 |
| N017269 | 2.89 | 1.46 | 2.13 | 2.38 | 2 | 1.97 | 2.01 |
| N018544 | 2.42 | 0.99 | 1.47 | 2.17 | 1.49 | 1.67 | 1.11 |
| N018552 | 2.28 | 0 | 0.15 | 0 | 0.52 | 0 | 0.47 |
| N020501 | 11.37 | | 2.61 | 2.9 | 2.34 | | |
| N045730 | 2.29 | 0.19 | 0.69 | 0.63 | 0.89 | 0.61 | 0.74 |
| N054582 | 1.84 | | 1.45 | 1.65 | 1.28 | | |
| N057046 | 5.59 | | 0.82 | 0 | 0.7 | | |
| N057054 | 21.05 | | 2.69 | 3.25 | 2.4 | | |
| N074598 | 2.53 | | 1.53 | 1.13 | 1.36 | | |
| N286613 | 4.11 | 2.38 | 2.54 | 3.3 | 2.56 | 3 | 3.83 |
| N286656 | 7.95 | 1.77 | 2.26 | 2.73 | 3.24 | 2.6 | 4.12 |
| N286680 | 4.58 | 2.75 | 2.86 | 3.3 | 2.85 | 3.39 | 1.45 |
| N318050 | 3.93 | 1.56 | 2.16 | | 2.18 | | 2.05 |
| N318341 | 4.46 | 1.72 | 2.38 | 2.86 | 2.12 | 2.4 | 1.86 |
| N318384 | 1.63 | 0.6 | 1.19 | 1.29 | 1.12 | 1.18 | 0.71 |
| N318421 | 3.86 | 0.69 | 1.15 | 1.45 | 1.47 | 1.14 | 1.56 |
| N329630 | 6.9 | 1.24 | 1.69 | 2.34 | 2.28 | 1.82 | 4.04 |
| N376488 | 4.73 | 0.64 | 1.2 | 1.3 | 1.57 | 1.14 | 1.57 |
| N376912 | 2.55 | 0.27 | 0.84 | 0.94 | 1.15 | 0.8 | 1.07 |
| N40776- | 3.46 | 0.62 | 1 | 0.98 | 1.35 | 1.15 | 1.21 |
| N418599 | 2.6 | 1.11 | 1.46 | 1.94 | 1.49 | 1.63 | 2.01 |
| N46043- | 4.18 | 0.67 | 1.34 | 1.18 | 1.72 | 1.03 | 0.9 |
| N461993 | 2.92 | 0 | 0.16 | 0.01 | 0.69 | 0 | 0.73 |
| N462187 | 3.96 | 0.79 | 1.32 | 1.18 | 1.79 | 1.43 | 1.23 |
| N483535 | 6.42 | 0 | 0.3 | 0 | 1.28 | 0 | 0.83 |
| N491678 | 7.73 | | 3.86 | 3.38 | 3.43 | | |
| N494801 | 4.38 | | 2.96 | 2.64 | 2.65 | | |
| N511498 | 2.24 | 0.46 | 0.81 | 0.71 | 1.03 | 0.78 | 0.51 |
| N520547 | 7.74 | | 3.03 | 3.74 | 2.7 | | |
| N527039 | 2.36 | 0.31 | 0.79 | 0.41 | 1.03 | 0.7 | 0.6 |
| N530485 | 6.8 | 0 | 0.32 | 0 | 1.4 | 0 | 0.66 |
| N593116 | 2.38 | 0.99 | 1.41 | 1.95 | 1.42 | 1.49 | 1.46 |
| N734641 | 3.04 | | 8.3 | 7.31 | 7.23 | | |

TABLE 4-continued

LFABP assays in ng/ml obtained with the Hycult biotechnology commercial test and with the different developed Vidas ® tests

| Patient | Hycult | 2C9G6/ 5A8H2 | 5A8H2/ 3D6G1 | 2C9G6/ 2E5G9 | 3A7B4/ 3D6G1 | 3D6G1/5A8H2 | 8B10B8/ 5A8H2 |
|---|---|---|---|---|---|---|---|
| N748022 | 2.14 | 0 | 0.17 | 0 | 0.46 | 0 | 0.47 |
| N828353 | 8.21 | | 4.52 | 4.11 | 4.01 | | |
| N831245 | 7.74 | | 2.77 | 2.32 | 2.48 | | |
| N862300 | 3.59 | 1.79 | 4.75 | | 3.53 | | 2.33 |

Correlations of these different tests compared to the 2C9G6/5A8H2 test are reported in Table 5 below.

TABLE 5

Data of correlation between different ELISA tests

| Parameter | 5A8H2/3D6G1 | 2C9G6/2E5G9 | 3A7B4/3D6G1 | 3D6G1/5A8H2 | 8B10B8/5A8H2 | Hycult |
|---|---|---|---|---|---|---|
| Number of XY Pairs | 47 | 45 | 47 | 45 | 47 | 47 |
| Spearman r | 0.9864 | 0.9783 | 0.9244 | 0.9909 | 0.8091 | 0.5298 |
| 95% confidence interval | 0.9752 to 0.9926 | 0.9598 to 0.9883 | 0.8653 to 0.9581 | 0.9831 to 0.9951 | 0.6752 to 0.8914 | 0.2781 to 0.713 |
| P value (two-tailed) | <0.0001 | <0.0001 | <0.0001 | <0.0001 | <0.0001 | 0.0001 |
| Is the correlation significant? (alpha = 0.05) | Yes | Yes | Yes | Yes | Yes | Yes |

The different tests developed in Vidas® have a good correlation between them and may be used to assay LFABP protein.

EXAMPLE 3

Detection of Adenomas Patients by ELISA Assay of LFABP on Vidas® Automaton

1) Patients and Samples

The collection of blood samples was carried out through a network of 8 clinical centers distributed throughout France, within the framework for 2 Huriet law protocols for patients suffering from colorectal cancer. For control patients, negative coloscopies and holders of colorectal adenomas, a multicenter study involving about thirty gastroenterologists was provided to collect the blood of Hemocult™ positive patients before carrying out coloscopy and any bowel preparation.

All samples were carried out in accordance with the legislation in force and the Good Clinical Practices, following a process of storage and follow-up in accordance with good laboratory practices, samples from patients and negative coloscopies controls being collected exactly under the same conditions.

To obtain serum, the blood sample is carried out on dry tube. After coagulation, the tube is centrifuged 10 min at 1000 g, the serum is collected, aliquoted and kept at −80° C. The samples are perfectly documented for the clinical history of patients.

A total of 147 patients was tested: 70 control patients with a completely normal coloscopy (Coloneg), and 77 patients suffering from colorectal adenomas (high-grade or low-grade dysplasia).

Among 77 Adenomas:
24 are low-risk adenomas (low grade dysplasia and size <1 cm, and no villous component)
37 are high-risk adenomas without severe dysplasia (>=1 cm or presence of villous component)
16 are high-risk high-grade adenomas (severe dysplasia, whatever the size, with or without villous component).

2) Vidas® Assay LFABP, ACE and CA19-9

LFABP protein was assayed by LFABP Vidas® 2C9G6/5A8H2 test described in example 2. This type of test may be carried out also in microplate, in automated or manual way.

For this example, ELISA test was constructed by using the reagents of Vidas® HBs Ag Ultra Kit (bioMérieux, Cat. No. 30315).

The reagents were used as described in the corresponding note (ref 11728 D-FR-2005/05), with the following modifications The cones were sensitized with capture Ac 2C9G6 used at a concentration of 10 µg/ml.
The content of the second well of HBs Ag Ultra cartridge was replaced by 300 µl of revelation antibody 5A8H2, coupled with biotin, diluted to 1 µg/ml in the buffer of the second well of the Vidas® HBs Ag Ultra kit (buffer with goat serum and sodium azide 1 g/l).
The serum sample (50 µl) was diluted directly in the second well of HBs Ag Ultra cartridge.
ELISA reaction was carried out by means of Vidas® automaton and HBS protocol whose step of incubation of the sample with the capture and revelation antibodies had been brought to 100 cycles.
The results were obtained as crude values after subtraction of the background noise (reading of the substrate before reaction).

Tumor markers CEA and CA19-9 were assayed by means of assay kits of the Applicant, respectively Vidas® CEAs, Vidas® CA19-9, following the operating protocol specific to each kit.

A standard curve was established by assaying a range of concentrations of the recombinant biomarker protein. The standard curve was plotted by reporting on the abscissa the concentration of the biomarker protein and on the ordinate the signal read by Vidas® (RFV or Relative Fluorescence Value). The concentration of the biomarker protein present in the body fluid to be assyed (blood, serum, plasma, stool) was calculated by plotting the corresponding concentration to the RFV signal read by Vidas®.

TABLE 6

Serum assays of LFABP, ACE and CA-19-9 in adenomas patients and negative coloscopies controls (ColoNeg)

| Pathology | Patient N° | Age | Sex | TNM Stage | ACE ng/mL | CA19-9 U/mL | LFABP ng/ml |
|---|---|---|---|---|---|---|---|
| ColoNeg | HGED005 | 68 | Man | NA | 2.08 | 4.38 | 3.7 |
| ColoNeg | PROMISED 21-01-005 | 68 | Man | NA | 0.5 | 16.94 | 5.94 |
| ColoNeg | PROMISED 21-01-006 | 62 | Man | NA | 0 | 2.1 | 2.65 |
| ColoNeg | PROMISED 21-01-009 | 51 | Woman | NA | 0.68 | 10.36 | 9.52 |
| ColoNeg | PROMISED 21-01-011 | 60 | Woman | NA | 0 | 4.31 | 0.45 |
| ColoNeg | PROMISED 21-01-012 | 55 | Woman | NA | 2.1 | 9.02 | 1.94 |
| ColoNeg | PROMISED 21-02-001 | 73 | Woman | NA | 1.15 | 5.02 | 11.06 |
| ColoNeg | PROMISED 21-02-003 | 55 | Woman | NA | 0.81 | 19.93 | 3.38 |
| ColoNeg | PROMISED 21-02-004 | 57 | Man | NA | 0 | 2.48 | 7.23 |
| ColoNeg | PROMISED 21-02-006 | 51 | Man | NA | 0 | 3.67 | 4.47 |
| ColoNeg | PROMISED 21-02-008 | 55 | Man | NA | 1.1 | 7.61 | 10.22 |
| ColoNeg | PROMISED 21-02-011 | 55 | Woman | NA | 1.56 | 13.65 | 2.01 |
| ColoNeg | PROMISED 21-02-014 | 58 | Man | NA | 0.81 | 2.02 | 6.68 |
| ColoNeg | PROMISED 21-02-016 | 62 | Man | NA | 3.36 | 3.43 | 0.43 |
| ColoNeg | PROMISED 21-03-004 | 61 | Man | NA | 3.46 | 2.33 | 8.62 |
| ColoNeg | PROMISED 21-03-013 | 52 | Woman | NA | 0 | 1.02 | 2.98 |
| ColoNeg | PROMISED 21-03-015 | 74 | Woman | NA | 0.9 | 2.48 | 7.26 |
| ColoNeg | PROMISED 21-04-002 | 67 | Man | NA | 0.83 | 9.73 | 5.97 |
| ColoNeg | PROMISED 21-04-006 | 72 | Man | NA | 0.68 | 2.33 | 2.25 |
| ColoNeg | PROMISED 21-04-007 | 68 | Woman | NA | 0.79 | 3.04 | 7.26 |
| ColoNeg | PROMISED 21-04-008 | 62 | Woman | NA | 1.06 | 1.02 | 5.97 |
| ColoNeg | PROMISED 21-04-009 | 58 | Man | NA | 1.1 | 11.92 | 3.67 |
| ColoNeg | PROMISED 21-04-013 | 63 | Woman | NA | 3.09 | 11.92 | 5.03 |
| ColoNeg | PROMISED 21-07-004 | 66 | Man | NA | 1.33 | 3.83 | 9.55 |
| ColoNeg | PROMISED 21-12-007 | 53 | Woman | NA | 0 | 2.86 | 6.03 |
| ColoNeg | PROMISED 21-12-011 | 52 | Man | NA | 4.24 | 8.63 | 1.79 |
| ColoNeg | PROMISED 21-22-001 | 61 | Woman | NA | 2.87 | 17.25 | 2.08 |
| ColoNeg | PROMISED 21-22-006 | 65 | Woman | NA | 1.06 | 2.33 | 6.6 |
| ColoNeg | PROMISED 21-22-008 | 57 | Woman | NA | 0 | 2.79 | 5.2 |
| ColoNeg | PROMISED 37-03-004 | 53 | Woman | NA | 0.74 | 2.17 | 2.18 |
| ColoNeg | PROMISED 37-04-001 | 62 | Man | NA | 5.16 | 4.54 | 7.09 |
| ColoNeg | PROMISED 37-04-005 | 69 | Woman | NA | 0.92 | 3.51 | 6.51 |
| ColoNeg | PROMISED 37-05-008 | 55 | Man | NA | 0 | 2.86 | 6.6 |
| ColoNeg | PROMISED 37-06-001 | 65 | Woman | NA | 1.49 | 5.65 | 5.99 |
| ColoNeg | PROMISED 37-09-002 | 50 | Woman | NA | 0.77 | 26 | 1.74 |
| ColoNeg | PROMISED 37-11-001 | 56 | Man | NA | 0 | 1.63 | 2.72 |
| ColoNeg | PROMISED 37-11-002 | 59 | Man | NA | 0 | 1.86 | 2.4 |
| ColoNeg | PROMISED 37-11-011 | 71 | Man | NA | 1.28 | 0.48 | 4.69 |
| ColoNeg | PROMISED 37-11-016 | 50 | Woman | NA | 0 | 5.02 | 1.87 |
| ColoNeg | PROMISED 37-12-002 | 63 | Man | NA | 0.79 | 2.63 | 3.01 |
| ColoNeg | PROMISED 37-13-003 | 53 | Woman | NA | 0.92 | 7.38 | 4.28 |
| ColoNeg | PROMISED 37-13-006 | 53 | Man | NA | 0.88 | 1.48 | 8.85 |
| ColoNeg | PROMISED 37-13-008 | 61 | Man | NA | 0 | 0.94 | 4.22 |
| ColoNeg | PROMISED 37-14-009 | 63 | Man | NA | 0.97 | 0.64 | 8.69 |
| ColoNeg | PROMISED 37-14-018 | 60 | Man | NA | 0.57 | 2.86 | 6.11 |
| ColoNeg | PROMISED 37-14-021 | 61 | Woman | NA | 0.92 | 3.59 | 0.62 |
| ColoNeg | PROMISED 37-15-002 | 68 | Woman | NA | 0.68 | 3.75 | 3.15 |
| ColoNeg | PROMISED 37-15-006 | 67 | Woman | NA | 1.08 | 2.1 | 6.3 |
| ColoNeg | PROMISED 37-16-001 | 57 | Man | NA | 0.74 | 3.75 | 3.99 |
| ColoNeg | PROMISED 37-17-001 | 52 | Man | NA | 1.87 | 4.78 | 4.63 |
| ColoNeg | PROMISED 37-17-003 | 55 | Man | NA | 5.81 | 1.71 | 2.65 |
| ColoNeg | PROMISED 37-17-004 | 58 | Woman | NA | 1.01 | 3.04 | 5.68 |
| ColoNeg | PROMISED 37-18-001 | 53 | Man | NA | 0.55 | 3.43 | 4.31 |
| ColoNeg | PROMISED 37-18-003 | 50 | Woman | NA | 0.63 | 2.33 | 7.76 |
| ColoNeg | PROMISED 37-18-004 | 57 | Man | NA | 0 | 2.1 | 3.83 |
| ColoNeg | PROMISED 37-18-005 | 55 | Woman | NA | 0.85 | 3.28 | 3.49 |
| ColoNeg | PROMISED 37-18-024 |  | Man | NA | 1.1 | 4.38 | 2.55 |
| ColoNeg | PROMISED 37-19-006 | 50 | Man | NA | 0 | 1.63 | 9.08 |
| ColoNeg | PROMISED 37-19-007 | 51 | Woman | NA | 0.66 | 0.56 | 3.33 |
| ColoNeg | PROMISED 37-20-004 | 53 | Woman | NA | 1.17 | 1.02 | 2.84 |
| ColoNeg | PROMISED 71-02-003 | 60 | Woman | NA | 0.55 | 1.33 | 1.62 |
| ColoNeg | PROMISED 71-04-003 | 75 | Woman | NA | 0.57 | 5.57 | 6.93 |
| ColoNeg | PROMISED 71-09-007 | 52 | Man | NA | 0.88 | 4.86 | 4.81 |
| ColoNeg | PROMISED 71-10-001 | 56 | Woman | NA | 1.15 | 15.14 | 2.15 |
| ColoNeg | PROMISED 71-10-007 | 71 | Woman | NA | 2.8 | 3.2 | 0.82 |
| ColoNeg | PROMISED 71-11-001 | 63 | Man | NA | 1.45 | 3 | 3.44 |
| ColoNeg | PROMISED 71-11-003 | 59 | Woman | NA | 1.26 | 40.93 | 3.91 |
| ColoNeg | PROMISED 71-11-006 | 59 | Man | NA | 0.66 | 2.33 | 4.22 |
| ColoNeg | PROMISED 71-11-008 | 54 | Man | NA | 0.88 | 8.32 | 2.59 |
| ColoNeg | PROMISED 71-11-009 | 60 | Woman | NA | 0.5 | 7.3 | 5.82 |
| Adenoma | GHAB007 | 67 | Man | NA | 2.65 | 6.89 | 4.12 |
| Adenoma | GHAB028 | 77 | Man | NA | 1.79 | 3.53 | 13.02 |
| Adenoma | GHAB046 | 54 | Man | NA | 3.07 | 5.97 | 5.09 |
| Adenoma | GHAB054 | 62 | Man | NA | 1.22 | 3 | 2.09 |
| Adenoma | GHBD079 | 76 | Man | NA | 5.87 | 8.08 | 3.49 |

TABLE 6-continued

Serum assays of LFABP, ACE and CA-19-9 in adenomas patients and negative coloscopies controls (ColoNeg)

| Pathology | Patient N° | Age | Sex | TNM Stage | ACE ng/mL | CA19-9 U/mL | LFABP ng/ml |
|---|---|---|---|---|---|---|---|
| Adenoma | HGED009 | 68 | Woman | NA | 1.45 | 4.55 | 4.12 |
| Adenoma | HGED013 | 59 | Man | NA | 1.18 | 3 | 4.65 |
| Adenoma | HGED019 | 52 | Man | NA | 1.67 | 3 | 1.76 |
| Adenoma | HGED038 | 58 | Man | NA | 2.18 | 3 | 11.29 |
| Adenoma | HGED046 | 57 | Man | NA | 2.09 | 3 | 20.4 |
| Adenoma | PROMISED 21-01-008 | | | NA | 0.55 | 3 | 2.14 |
| Adenoma | PROMISED 21-02-012 | 50 | Man | NA | 1.2 | 3 | 13.31 |
| Adenoma | PROMISED 21-08-004 | 69 | Woman | NA | 1.26 | 3 | 2.65 |
| Adenoma | PROMISED 21-22-016 | 68 | Woman | NA | 0.76 | 3 | 3.63 |
| Adenoma | PROMISED 21-22-019 | 68 | Woman | NA | 0.5 | 3.28 | 3.88 |
| Adenoma | PROMISED 37-03-008 | 53 | Man | NA | 1.91 | 3 | 12.35 |
| Adenoma | PROMISED 37-03-011 | 62 | Man | NA | 0.5 | 3 | 4.92 |
| Adenoma | PROMISED 37-05-012 | 71 | Woman | NA | 0.78 | 3 | 3.57 |
| Adenoma | PROMISED 37-08-001 | 64 | Woman | NA | 1.24 | 3 | 9.82 |
| Adenoma | PROMISED 37-09-001 | 56 | Woman | NA | 7.08 | 3 | 3.63 |
| Adenoma | PROMISED 37-11-003 | 70 | Man | NA | 2.14 | 3 | 6.83 |
| Adenoma | PROMISED 37-11-008 | 51 | Man | NA | 1.06 | 3.53 | 3.14 |
| Adenoma | PROMISED 37-11-015 | 69 | Man | NA | 2.67 | 3 | 10.56 |
| Adenoma | PROMISED 37-11-018 | 57 | Man | NA | 1.61 | 29.05 | 7.95 |
| Adenoma | PROMISED 37-13-002 | 59 | Man | NA | 1.71 | 3 | 4.65 |
| Adenoma | PROMISED 37-14-002 | 53 | Man | NA | 1.57 | 3 | 3.73 |
| Adenoma | PROMISED 37-14-003 | 63 | Woman | NA | 1.45 | 3 | 8.05 |
| Adenoma | PROMISED 37-14-008 | 52 | Woman | NA | 0.55 | 3 | 0.89 |
| Adenoma | PROMISED 37-15-004 | 58 | Man | NA | 3.18 | 9.3 | 1.59 |
| Adenoma | PROMISED 37-15-005 | 72 | Man | NA | 3.07 | 3 | 0.68 |
| Adenoma | PROMISED 37-20-003 | 64 | Man | NA | 2.91 | 3 | 13.31 |
| Adenoma | PROMISED 37-23-001 | 52 | Man | NA | 3.84 | 9.92 | 4.72 |
| Adenoma | PROMISED 37-23-004 | 71 | Woman | NA | 1.08 | 10.2 | 4.31 |
| Adenoma | PROMISED 71-08-008 | 51 | Man | NA | 1.24 | 3 | 7.08 |
| Adenoma | PROMISED 71-10-002 | 62 | Man | NA | 2.37 | 18.29 | 1.09 |
| Adenoma | PROMISED 71-10-004 | 63 | Man | NA | 2.01 | 3.77 | 3.04 |
| Adenoma | PROMISED 71-11-002 | 75 | Man | NA | 2.47 | 6.02 | 26.32 |
| Adenoma | CLSP350 | 76 | Man | NA | 7.03 | 3 | 3.05 |
| Adenoma | CLSP398 | 43 | Woman | NA | 1.32 | 3 | 4.82 |
| Adenoma | CLSP427 | 83 | Man | NA | 3.11 | 7.99 | 11.24 |
| Adenoma | CLSP457 | 66 | Man | NA | 10.92 | 3 | 11.36 |
| Adenoma | CLSP681 | 61 | Woman | NA | 0.76 | 8.27 | 26.13 |
| Adenoma | CLSP769 | 50 | Woman | NA | 0.5 | 3 | 44.76 |
| Adenoma | GHBD014 | 71 | Man | NA | 1.95 | 4.13 | 24.03 |
| Adenoma | GHBD053 | 66 | Woman | NA | 0.85 | 3 | 4.56 |
| Adenoma | PROMISED 21-02-007 | | | NA | 0.61 | 3 | 8.56 |
| Adenoma | PROMISED 21-02-009 | | | NA | 3.22 | 7.93 | 7.09 |
| Adenoma | PROMISED 21-02-017 | 64 | Man | NA | 1.49 | 3 | 1.83 |
| Adenoma | PROMISED 21-03-001 | 58 | Man | NA | 2.09 | 3 | 7.32 |
| Adenoma | PROMISED 21-03-017 | 69 | Man | NA | 1.57 | 5.44 | 4.52 |
| Adenoma | PROMISED 21-08-001 | 52 | Man | NA | 3.26 | 11.66 | 3.71 |
| Adenoma | PROMISED 37-03-003 | 57 | Man | NA | 0.97 | 3 | 5.98 |
| Adenoma | PROMISED 37-03-006 | 60 | Woman | NA | 0.5 | 14.27 | 0.5 |
| Adenoma | PROMISED 37-06-003 | 60 | Woman | NA | 0.64 | 3 | 1.82 |
| Adenoma | PROMISED 37-09-004 | 74 | Man | NA | 2.18 | 5.61 | 10.2 |
| Adenoma | PROMISED 37-11-005 | 54 | Woman | NA | 0.53 | 3 | 3.2 |
| Adenoma | PROMISED 37-13-007 | 65 | Woman | NA | 0.93 | 3 | 3.53 |
| Adenoma | PROMISED 37-14-015 | 74 | Woman | NA | 1.45 | 8.39 | 1.88 |
| Adenoma | PROMISED 37-19-001 | 71 | Man | NA | 1.77 | 5.44 | 4.53 |
| Adenoma | PROMISED 37-23-003 | 67 | Woman | NA | 0.82 | 5.67 | 5.18 |
| Adenoma | PROMISED 71-10-012 | 50 | Man | NA | 0.66 | 3 | 12.36 |
| Adenoma | CLSP022 | 70 | Man | NA | 200 | 3 | 0.71 |
| Adenoma | CLSP036 | 70 | Man | NA | 0.91 | 3 | 7.73 |
| Adenoma | CLSP270 | 75 | Man | NA | 1.2 | 3 | 10.36 |
| Adenoma | CLSP287 | 56 | Woman | NA | 1.2 | 3.16 | 2.83 |
| Adenoma | CLSP337 | 63 | Woman | NA | 0.61 | 1.71 | 14.47 |
| Adenoma | CLSP358 | 73 | Man | NA | 2.09 | 22.23 | 5.48 |
| Adenoma | CLSP359 | 60 | Man | NA | 1.65 | 17.96 | 6.58 |
| Adenoma | CLSP362 | 81 | Man | NA | 1.28 | 3 | 11.19 |
| Adenoma | CLSP378 | 75 | Man | NA | 0.63 | 2.1 | 3.93 |
| Adenoma | CLSP719 | 62 | Man | NA | 1.55 | 3 | 19.42 |
| Adenoma | CNSE018 | 75 | Woman | NA | 0.5 | 3 | 7.42 |

TABLE 6-continued

Serum assays of LFABP, ACE and CA-19-9 in adenomas patients and negative coloscopies controls (ColoNeg)

| Pathology | Patient N° | Age | Sex | TNM Stage | ACE ng/mL | CA19-9 U/mL | LFABP ng/ml |
|---|---|---|---|---|---|---|---|
| Adenoma | GESE003 | 59 | Woman | NA | 0.5 | 3 | 2.46 |
| Adenoma | GHAB004 | 84 | Man | NA | 4.17 | 4.79 | 5.8 |
| Adenoma | GHBD002 | 87 | Man | NA | 0.61 | 3 | 4.28 |
| Adenoma | PROMISED 21-22-004 | 71 | Woman | NA | 2.73 | 21.25 | 3.62 |
| Adenoma | PROMISED 71-10-006 | 57 | Man | NA | 4.74 | 18.84 | 9.59 |
| | Threshold (max concentration of the ColoNeg) | | | | 5.81 | 40.93 | 11.06 |
| | Adenomas higher than the threshold | | | | 4 | 0 | 16 |

The assay results of LFABP are shown in FIG. 1.

With LFABP threshold 11.06 ng/ml (the highest rate for ColoNeg controls, namely a specificity of 100%), 16 adenoma patients were detected on 77, namely 20.5% of sensitivity for adenomas, high risk and low risk combined. High risk being defined by the size >=1 cm, the presence of a severe dysplasia or the presence of a villous component.

To know the predictive value which adenoma detection test would have, one must have to have the prevalence of the disease.

According to the studies (autopsy, systematic coloscopies, post blood evaluation in the feces), the prevalence of adenomas varies a little. In a recent study published in JAMA [Ferlitsch et al, Sex-Specific Prevalence of Adenomas, Advanced Adenomas, and Colorectal Cancer in Individuals Undergoing Screening Colonoscopy JAMA, Sep. 28, 2011—Vol 306, No. 12], the prevalence of all adenomas is described at 19.7%, and that of advanced adenomas at 6.3%, but in this same study the prevalence of cancer is 1.1%, which is the double of what is described in Europe (perhaps due to a screening coloscopy: not only asymptomatic subjects). The definition of advanced adenomas is perhaps different from that we used.

In an autopsy study [Williams A R, Balasooriya B A, Day D W. Polyps and cancer of the large bowel: a necropsy study in Liverpool. Gut. 1982 October; 23(10):835-42], the prevalence was described at 33% for adenomas and at 13% for advanced adenomas.

Based on the above results, by setting the threshold at 11.06 ng/ml to keep the same threshold for carcinomas in situ T0, 20.5% of adenomas is detected. A positive predictive value of LFABP test for the detection of adenomas may be extrapolated: from 50% to 62% according to the used prevalence figures (for a fixed specificity at 95%).

Thus, the positive predictive value (PPV) of LFABP assay in the serum of patients, for detecting adenomas, is good. Particularly, PPV is as good as that described for tests of the blood in feces (digits of VPP in the literature are from 34 to 43% for advanced adenomas according to tests of blood research in the used feces, on screening studies carried out with immunological tests for blood research in the feces, and around 13% to 20% for guaiac tests).

CAE assay results (on CEAs Vidas®) for detecting adenomas patients:

Comparatively, only 4 adenomas patients have CEA level above the threshold of negative coloscopy controls (6.05 ng/ml in our cohort, described to be between 5 and 10 ng/ml). Only 2 patients have CEA level>10 ng/ml on the 77 tested adenomas patients.

Results the CA19-9 assay (on CA19-0 Vidas®) for detecting adenomas patients:

There is no adenoma patient with a CA-19-9 level above the threshold of negative coloscopies. For adenomas patients, the highest level is of 29.05 U/ml.

EXAMPLE 4

Detection of Tumors In Situ (T0) by ELISA Assay of LFABP on Vidas® Automaton

1) Patients and Samples

The collection of blood samples was carried out through a network of 8 clinical centers distributed throughout France, within the framework of 2 Huriet law protocols for patients suffering from colorectal cancer and tumors in situ. For control patients, negative coloscopies, and holders of colorectal adenomas, a multicenter study involving about thirty gastroenterologists was made to collect the blood of Hemoccult™ positive patients, before carrying out coloscopy and any other bowel preparation. Furthermore, serum samples were obtained from blood donors of French Blood Establishments (EFS), following the procedures in practice in these centers.

All samples were carried out in accordance with the legislation in force and the Good Clinical Practices, following a process of storage and follow-up in accordance with good laboratory practices, samples from patients and negative coloscopies controls being collected exactly under the same conditions.

To obtain serum, the blood sample is carried out on dry tube. After coagulation, the tube is centrifuged 10 min at 1000 g, the serum is collected, aliquoted and kept at −80° C. The samples are perfectly documented for the clinical history of patients.

A total of 182 patients was tested: 8 patients presenting a tumor in situ T0, 104 patients presenting an invasive colorectal cancer of TNM stage I to IV, 70 control patients with a totally normal coloscopy.

- 8 patients with Tis (tumor in situ, or intra-mucosal carcinoma, noninvasive (T0, N0, M0 at the time of blood collection)
- 14 invasive CRC patients of TNM stage I
- 49 invasive CRC patients of TNM stage II
- 27 invasive CRC patients of TNM stage III
- 13 invasive CRC patients of TNM stage IV
- 1 not rated CRC patient 2) Vidas® Assay LFABP protein was assayed by means of LFABP Vidas® 2C9G6/5A8H2 test described in example 2. This type of test may also be carried out in microplate, in automated or manual way.

For this example, ELISA test was constructed by using the reagents of Vidas® HBs Ag Ultra kit (bioMérieux, Cat. No.

30315). The reagents were used as described in the corresponding note (ref. 11728 D-FR-2005/05.), modified as follows:
- The cones were sensitized with 2C9G6 capture Ac used at a concentration of 10 µg/ml.
- The content of the second well of HBs Ag Ultra cartridge was replaced by 300 µl of revelation antibody 5A8H2, coupled with biotin, diluted to 1 µg/ml in the buffer of the second well of the HBs Ag Ultra Vidas® kit (buffer with goat serum and sodium azide 1 g/l).
- The serum sample (50 µl) was diluted directly in the second well of HBs Ag Ultra cartridge.
- ELISA reaction was carried out by means of Vidas® automaton and HBS protocol whose step of incubation of the sample with the capture and revelation antibodies had been brought to 100 cycles.
- The results were obtained in the form of crude values after subtraction of the background noise (reading of the substrate before reaction).

Tumor markers CEA and CA19-9 were assayed by means of assay kits of the Applicant, respectively Vidas® CEAS, Vidas® CA19-9, following the operating protocol specific to each kit.

A standard curve was established by assaying a range of concentrations of the recombinant biomarker protein. The standard curve was plotted by reporting on the abscissa the concentration of the biomarker protein, and on the ordinate the signal read by Vidas® (RFV or Relative Fluorescence Value). The concentration of the biomarker protein presents in the body fluid to be assayed (blood, serum, plasma, feces) was calculated by plotting the concentration corresponding to the RFV signal read by Vidas®.

Tumor markers CEA and CA19-9 were assayed by assay kits of the Applicant, respectively Vidas® CEAs, Vidas® CA19-9, following the operating protocol specific to each kit.

TABLE 7

LFABP, ACE and CA19-9 assays of 182 tested patients

| Pathology | Patient N° | Age | Sex | TNM stage | Note | ACE ng/mL | CA19-9 ng/mL | LFABP ng/mL |
|---|---|---|---|---|---|---|---|---|
| ColoNeg | HGED005 | 68 | Man | NA | | 2.08 | 4.38 | 3.7 |
| ColoNeg | PROMISED 21-01-005 | 68 | Man | NA | | 0.5 | 16.94 | 5.94 |
| ColoNeg | PROMISED 21-01-006 | 62 | Man | NA | | 0 | 2.1 | 2.65 |
| ColoNeg | PROMISED 21-01-009 | 51 | Woman | NA | | 0.68 | 10.36 | 9.52 |
| ColoNeg | PROMISED 21-01-011 | 60 | Woman | NA | | 0 | 4.31 | 0.45 |
| ColoNeg | PROMISED 21-01-012 | 55 | Woman | NA | | 2.1 | 9.02 | 1.94 |
| ColoNeg | PROMISED 21-02-001 | 73 | Woman | NA | | 1.15 | 5.02 | 11.06 |
| ColoNeg | PROMISED 21-02-003 | 55 | Woman | NA | | 0.81 | 19.93 | 3.38 |
| ColoNeg | PROMISED 21-02-004 | 57 | Man | NA | | 0 | 2.48 | 7.23 |
| ColoNeg | PROMISED 21-02-006 | 51 | Man | NA | | 0 | 3.67 | 4.47 |
| ColoNeg | PROMISED 21-02-008 | 55 | Man | NA | | 1.1 | 7.61 | 10.22 |
| ColoNeg | PROMISED 21-02-011 | 55 | Woman | NA | | 1.56 | 13.65 | 2.01 |
| ColoNeg | PROMISED 21-02-014 | 58 | Man | NA | | 0.81 | 2.02 | 6.68 |
| ColoNeg | PROMISED 21-02-016 | 62 | Man | NA | | 3.36 | 3.43 | 0.43 |
| ColoNeg | PROMISED 21-03-004 | 61 | Man | NA | | 3.46 | 2.33 | 8.62 |
| ColoNeg | PROMISED 21-03-013 | 52 | Woman | NA | | 0 | 1.02 | 2.98 |
| ColoNeg | PROMISED 21-03-015 | 74 | Woman | NA | | 0.9 | 2.48 | 7.26 |
| ColoNeg | PROMISED 21-04-002 | 67 | Man | NA | | 0.83 | 9.73 | 5.97 |
| ColoNeg | PROMISED 21-04-006 | 72 | Man | NA | | 0.68 | 2.33 | 2.25 |
| ColoNeg | PROMISED 21-04-007 | 68 | Woman | NA | | 0.79 | 3.04 | 7.26 |
| ColoNeg | PROMISED 21-04-008 | 62 | Woman | NA | | 1.06 | 1.02 | 5.97 |
| ColoNeg | PROMISED 21-04-009 | 58 | Man | NA | | 1.1 | 11.92 | 3.67 |
| ColoNeg | PROMISED 21-04-013 | 63 | Woman | NA | | 3.09 | 11.92 | 5.03 |
| ColoNeg | PROMISED 21-07-004 | 66 | Man | NA | | 1.33 | 3.83 | 9.55 |
| ColoNeg | PROMISED 21-12-007 | 53 | Woman | NA | | 0 | 2.86 | 6.03 |
| ColoNeg | PROMISED 21-12-011 | 52 | Man | NA | | 4.24 | 8.63 | 1.79 |
| ColoNeg | PROMISED 21-22-001 | 61 | Woman | NA | | 2.87 | 17.25 | 2.08 |
| ColoNeg | PROMISED 21-22-006 | 65 | Woman | NA | | 1.06 | 2.33 | 6.6 |
| ColoNeg | PROMISED 21-22-008 | 57 | Woman | NA | | 0 | 2.79 | 5.2 |
| ColoNeg | PROMISED 37-03-004 | 53 | Woman | NA | | 0.74 | 2.17 | 2.18 |
| ColoNeg | PROMISED 37-04-001 | 62 | Man | NA | | 5.16 | 4.54 | 7.09 |
| ColoNeg | PROMISED 37-04-005 | 69 | Woman | NA | | 0.92 | 3.51 | 6.51 |
| ColoNeg | PROMISED 37-05-008 | 55 | Man | NA | | 0 | 2.86 | 6.6 |
| ColoNeg | PROMISED 37-06-001 | 65 | Woman | NA | | 1.49 | 5.65 | 5.99 |
| ColoNeg | PROMISED 37-09-002 | 50 | Woman | NA | | 0.77 | 26 | 1.74 |
| ColoNeg | PROMISED 37-11-001 | 56 | Man | NA | | 0 | 1.63 | 2.72 |
| ColoNeg | PROMISED 37-11-002 | 59 | Man | NA | | 0 | 1.86 | 2.4 |
| ColoNeg | PROMISED 37-11-011 | 71 | Man | NA | | 1.28 | 0.48 | 4.69 |
| ColoNeg | PROMISED 37-11-016 | 50 | Woman | NA | | 0 | 5.02 | 1.87 |
| ColoNeg | PROMISED 37-12-002 | 63 | Man | NA | | 0.79 | 2.63 | 3.01 |
| ColoNeg | PROMISED 37-13-003 | 53 | Woman | NA | | 0.92 | 7.38 | 4.28 |
| ColoNeg | PROMISED 37-13-006 | 53 | Man | NA | | 0.88 | 1.48 | 8.85 |
| ColoNeg | PROMISED 37-13-008 | 61 | Man | NA | | 0 | 0.94 | 4.22 |
| ColoNeg | PROMISED 37-14-009 | 63 | Man | NA | | 0.97 | 0.64 | 8.69 |
| ColoNeg | PROMISED 37-14-018 | 60 | Man | NA | | 0.57 | 2.86 | 6.11 |
| ColoNeg | PROMISED 37-14-021 | 61 | Woman | NA | | 0.92 | 3.59 | 0.62 |
| ColoNeg | PROMISED 37-15-002 | 68 | Woman | NA | | 0.68 | 3.75 | 3.15 |
| ColoNeg | PROMISED 37-15-006 | 67 | Woman | NA | | 1.08 | 2.1 | 6.3 |
| ColoNeg | PROMISED 37-16-001 | 57 | Man | NA | | 0.74 | 3.75 | 3.99 |
| ColoNeg | PROMISED 37-17-001 | 52 | Man | NA | | 1.87 | 4.78 | 4.63 |
| ColoNeg | PROMISED 37-17-003 | 55 | Man | NA | | 5.81 | 1.71 | 2.65 |
| ColoNeg | PROMISED 37-17-004 | 58 | Woman | NA | | 1.01 | 3.04 | 5.68 |

TABLE 7-continued

LFABP, ACE and CA19-9 assays of 182 tested patients

| | | | | | | | |
|---|---|---|---|---|---|---|---|
| ColoNeg | PROMISED 37-18-001 | 53 | Man | NA | 0.55 | 3.43 | 4.31 |
| ColoNeg | PROMISED 37-18-003 | 50 | Woman | NA | 0.63 | 2.33 | 7.76 |
| ColoNeg | PROMISED 37-18-004 | 57 | Man | NA | 0 | 2.1 | 3.83 |
| ColoNeg | PROMISED 37-18-005 | 55 | Woman | NA | 0.85 | 3.28 | 3.49 |
| ColoNeg | PROMISED 37-18-024 | | Man | NA | 1.1 | 4.38 | 2.55 |
| ColoNeg | PROMISED 37-19-006 | 50 | Man | NA | 0 | 1.63 | 9.08 |
| ColoNeg | PROMISED 37-19-007 | 51 | Woman | NA | 0.66 | 0.56 | 3.33 |
| ColoNeg | PROMISED 37-20-004 | 53 | Woman | NA | 1.17 | 1.02 | 2.84 |
| ColoNeg | PROMISED 71-02-003 | 60 | Woman | NA | 0.55 | 1.33 | 1.62 |
| ColoNeg | PROMISED 71-04-003 | 75 | Woman | NA | 0.57 | 5.57 | 6.93 |
| ColoNeg | PROMISED 71-09-007 | 52 | Man | NA | 0.88 | 4.86 | 4.81 |
| ColoNeg | PROMISED 71-10-001 | 56 | Woman | NA | 1.15 | 15.14 | 2.15 |
| ColoNeg | PROMISED 71-10-007 | 71 | Woman | NA | 2.8 | 3.2 | 0.82 |
| ColoNeg | PROMISED 71-11-001 | 63 | Man | NA | 1.45 | 3 | 3.44 |
| ColoNeg | PROMISED 71-11-003 | 59 | Woman | NA | 1.26 | 40.93 | 3.91 |
| ColoNeg | PROMISED 71-11-006 | 59 | Man | NA | 0.66 | 2.33 | 4.22 |
| ColoNeg | PROMISED 71-11-008 | 54 | Man | NA | 0.88 | 8.32 | 2.59 |
| ColoNeg | PROMISED 71-11-009 | 60 | Woman | NA | 0.5 | 7.3 | 5.82 |
| Tis | CLSP234 | 79 | Man | T0 | 1.45 | 2.33 | 11.29 |
| Tis | CLSP300 | 80 | Woman | T0 | 1.61 | 2.02 | 8.15 |
| Tis | CLSP315 | 58 | Man | T0 | 0.7 | 2.1 | 11.12 |
| Tis | CLSP367 | 78 | Man | T0 | 0.9 | 4.31 | 7.21 |
| Tis | CLSP724 | 48 | Man | T0 | 0.92 | 28.45 | 11.9 |
| Tis | CNSE003 | 83 | Woman | T0 | 0 | 5.65 | 17.82 |
| Tis | CNSE004 | 73 | Woman | T0 | 0 | 1.4 | 4.3 |
| Tis | GHBD015 | 82 | Man | T0 | 0.83 | 5.65 | 12.83 |
| CRC | CBSE001 | 69 | Woman | I | 4.06 | 3 | 14.92 |
| CRC | CBSE016 | 74 | Man | I | 6.79 | 1.25 | 17.36 |
| CRC | CLSP047 | 76 | Woman | I | 1.06 | 0.79 | 0.26 |
| CRC | CLSP162 | 63 | Woman | I | 0 | 0.71 | 6.22 |
| CRC | CLSP196 | 55 | Man | I | 3.71 | 8.95 | 10.3 |
| CRC | CLSP224 | 84 | Woman | I | 4.62 | 6.12 | 42.38 |
| CRC | CLSP235 | 71 | Woman | I | 0 | 3.43 | 2.63 |
| CRC | CLSP263 | 70 | Man | I | 1.1 | 30.04 | 8.05 |
| CRC | CLSP340 | 78 | Man | I | 1.28 | 3 | 3.85 |
| CRC | CLSP344 | 77 | Woman | I | 1.49 | 2.17 | 3.78 |
| CRC | CLSP364 | 81 | Woman | I | 1.24 | 4.62 | 1.42 |
| CRC | CLSP376 | 51 | Man | I | 1.17 | 12.63 | 2.58 |
| CRC | GHBD003 | 54 | Man | I | 0.99 | 2.56 | 0.88 |
| CRC | GHBD094 | 82 | Man | I | 1.12 | 9.18 | 8.08 |
| CRC | CLSP075 | 65 | Man | II | 0.74 | 2.71 | 5.19 |
| CRC | CLSP076 | 82 | Woman | II | 0.97 | 0.71 | 10.27 |
| CRC | CLSP080 | 74 | Woman | II | 0.59 | 4.23 | 0.89 |
| CRC | CLSP096 | 79 | Woman | II | 12.7 | 7.22 | 8.86 |
| CRC | CLSP110 | 67 | Woman | II | 0 | 2.25 | 10.41 |
| CRC | CLSP117 | 78 | Woman | II | 2.08 | 5.25 | 20.19 |
| CRC | CLSP130 | 81 | Man | II | 1.15 | 3.59 | 11.15 |
| CRC | CLSP133 | 78 | Woman | II | 0.7 | 3.59 | 3.52 |
| CRC | CLSP143 | 76 | Woman | II | 5.45 | 2.33 | 5.87 |
| CRC | CLSP147 | 83 | Man | II | 1.56 | 1.56 | 3.55 |
| CRC | CLSP154 | 76 | Woman | II | 11.04 | 8.4 | 6.33 |
| CRC | CLSP155 | 81 | Woman | II | 11.53 | 37.95 | 3.3 |
| CRC | CLSP157 | 45 | Woman | II | 0.7 | 1.48 | 8.47 |
| CRC | CLSP165 | 52 | Man | II | 0 | 2.33 | 5.64 |
| CRC | CLSP170 | 80 | Woman | II | 5.11 | 8 | 13.1 |
| CRC | CLSP173 | 49 | Woman | II | 0.66 | 8.79 | 0.61 |
| CRC | CLSP177 | 81 | Man | II | 1.47 | 29.49 | 8.63 |
| CRC | CLSP178 | 55 | Man | II | 20.68 | 8.95 | 101.48 |
| CRC | CLSP179 | 69 | Woman | II | 5.81 | 8.24 | 9.89 |
| CRC | CLSP186 | 69 | Inconnu | II | 1.45 | 2.94 | 13.47 |
| CRC | CLSP194 | 70 | Man | II | 1.01 | 1.79 | 19.11 |
| CRC | CLSP201 | 75 | Man | II | 2.51 | 0.71 | 16.22 |
| CRC | CLSP207 | 72 | Woman | II | 1.35 | 26 | 15.17 |
| CRC | CLSP209 | 38 | Woman | II | 0.97 | 2.63 | 17.92 |
| CRC | CLSP220 | 81 | Woman | II | 7.52 | 12.79 | 10.63 |
| CRC | CLSP222 | 81 | Man | II | 5.5 | 3.83 | 21.07 |
| CRC | CLSP236 | 69 | Man | II | 0 | 1.63 | 13.64 |
| CRC | CLSP253 | 61 | Woman | II | 1.54 | 2.48 | 6.64 |
| CRC | CLSP256 | 86 | Woman | II | 3.54 | 10.75 | 8.27 |
| CRC | CLSP280 | 62 | Man | II | 2.2 | 8.63 | 5.7 |
| CRC | CLSP296 | 56 | Man | II | 1.89 | 73.08 | 9.93 |
| CRC | CLSP310 | 81 | Man | II | 1.89 | 6.98 | 2.94 |
| CRC | CLSP327 | 84 | Man | II | 0.94 | 1.17 | 7.25 |
| CRC | CLSP333 | 87 | Man | II | 1.58 | 19.45 | 10.01 |
| CRC | CLSP341 | 45 | Man | II | 0.53 | 3.67 | 3.46 |
| CRC | CLSP346 | 66 | Man | II | 7.2 | 39.88 | 5.67 |
| CRC | CLSP347 | 49 | Woman | II | 7.41 | 1.25 | 6.43 |
| CRC | CLSP380 | 60 | Man | II | 0.7 | 3.04 | 7.83 |

TABLE 7-continued

LFABP, ACE and CA19-9 assays of 182 tested patients

| | | | | | | | |
|---|---|---|---|---|---|---|---|
| CRC | CNSE002 | 62 | Woman | II | 3.84 | 4.46 | 1.58 |
| CRC | GHBD021 | 71 | Woman | II | 0.53 | 1.94 | 1.04 |
| CRC | GHBD043 | 71 | Man | II | 2.27 | 9.18 | 5.78 |
| CRC | GHBD064 | 83 | Woman | II | 21.08 | 5.65 | 23.26 |
| CRC | GHBD066 | 82 | Woman | II | 0.57 | 1.94 | 6.98 |
| CRC | GHBD075 | 58 | Man | II | 2.53 | 1.86 | 6.34 |
| CRC | GHBD087 | 62 | Woman | II | 2.17 | 5.1 | 8.83 |
| CRC | GHBD090 | 59 | Man | II | 0.79 | 3.59 | 4.82 |
| CRC | GHBD096 | 62 | Woman | II | 3.04 | 1.71 | 6.8 |
| CRC | GHBD100 | 75 | Man | II | 2.08 | 4.94 | 10.82 |
| CRC | GHBD103 | 68 | Man | II | 1.06 | 3.2 | 10.41 |
| CRC | CBSE023 | 76 | Man | III | 2.27 | 9.34 | 11.1 |
| CRC | CLSP044 | 81 | Man | III | 74.1 | 4.31 | 4.69 |
| CRC | CLSP074 | 79 | Woman | III | 0.81 | 7.06 | 4.26 |
| CRC | CLSP078 | 72 | Woman | III | 0.57 | 2.33 | 21.69 |
| CRC | CLSP081 | 78 | Woman | III | 1.56 | 2.94 | 4.8 |
| CRC | CLSP098 | 61 | Man | III | 0.77 | 2.56 | 4.55 |
| CRC | CLSP174 | 77 | Man | III | 31.33 | 264.9 | 20.46 |
| CRC | CLSP227 | 52 | Man | III | 14.52 | 7.3 | 44.85 |
| CRC | CLSP233 | 59 | Man | III | 1.03 | 4.23 | 2.38 |
| CRC | CLSP255 | 42 | Woman | III | 0.85 | 65.91 | 30.53 |
| CRC | CLSP289 | 52 | Man | III | 0.9 | 2.17 | 8.3 |
| CRC | CLSP320 | 70 | Man | III | 1.7 | 3.04 | 3.62 |
| CRC | CLSP324 | 53 | Man | III | 4.57 | 15.37 | 2.02 |
| CRC | CLSP383 | 78 | Man | III | 1.84 | 1.79 | 1.2 |
| CRC | CLSP384 | 37 | Man | III | 68.52 | 26.63 | 15.7 |
| CRC | CNSE001 | 78 | Man | III | 6.45 | 40.28 | 5.87 |
| CRC | CNSE016 | 65 | Man | III | 20.59 | 91.16 | 52.41 |
| CRC | CNSE017 | 77 | Woman | III | 0.61 | 2.17 | 16.79 |
| CRC | CSEM015 | 65 | Woman | III | 1.38 | 1.02 | 11.51 |
| CRC | CSEM029 | 63 | Woman | III | 2.13 | 3.67 | 5.65 |
| CRC | GHBD004 | 58 | Man | III | 16.26 | 5.73 | 1.97 |
| CRC | GHBD017 | 70 | Man | III | 0.68 | 3.99 | 0.91 |
| CRC | GHBD034 | 48 | Woman | III | 0.57 | 2.94 | 0.52 |
| CRC | GHBD042 | 77 | Woman | III | 0.5 | 13.88 | 5.95 |
| CRC | GHBD045 | 73 | Man | III | 0.55 | 1.56 | 1.07 |
| CRC | GHBD089 | 54 | Woman | III | 24.47 | 10.12 | 6.99 |
| CRC | GHBD105 | 79 | Man | III | 1.35 | 37.39 | 5.84 |
| CRC | CBSE012 | 37 | Woman | IV | 4.06 | 44.73 | 4.48 |
| CRC | CBSE026 | 72 | Man | IV | 333.4 | 23878 | 28.35 |
| CRC | CLSP156 | 59 | Man | IV | 14 | 43.27 | 8.75 |
| CRC | CLSP159 | 69 | Woman | IV | 44.38 | 164.91 | 9.74 |
| CRC | CLSP167 | 81 | Man | IV | 1.89 | 35.39 | 1.8 |
| CRC | CLSP260 | 57 | Woman | IV | 29.97 | 17.73 | 70.03 |
| CRC | CLSP334 | 54 | Woman | IV | 1.7 | 3.83 | 3.32 |
| CRC | CLSP357 | 78 | Man | IV | 9.37 | 76.31 | 4.52 |
| CRC | CLSP365 | 64 | Man | IV | 29.5 | 1135.2 | 6.41 |
| CRC | CLSP366 | 45 | Man | IV | 2.63 | 52.4 | 4.62 |
| CRC | GHBD022 | 56 | Man | IV | 1369.5 | 21.58 | 20.22 |
| CRC | GHBD071 | 61 | Man | IV | 38.02 | 41.09 | 34.61 |
| CRC | GHBD093 | 78 | Man | IV | 0 | 6.91 | 4.44 |
| CRC | CLSP197 | 68 | Woman | NA | 0.59 | 10.12 | 7.23 |
| Threshold (max concentration of the ColoNeg) | | | | | 5.81 | 40.93 | 11.06 |
| Tumor in situ Tis T0: Number of patients higher than the threshold | | | | | 0 | 0 | 5 |

| | LFABP Number of detected patients | ACE Number of detected patients | CA 19-9 Number of detected patients | Total number |
|---|---|---|---|---|
| Tis T0 | 5 | 0 | 0 | n = 8 |
| CRC + stage I | 3 | 1 | 0 | n = 14 |
| CRC + stage II | 13 | 8 | 1 | n = 49 |
| CRC + stage III | 10 | 9 | 3 | n = 27 |
| CRC + stage IV | 5 | 8 | 8 | n = 14 |

| | LFABP | ACE | CA19-9 |
|---|---|---|---|
| sensitivity Tis T0/ColoNeg in percent | 63 | 0 | 0 |
| sensitivity stage I CRC/ColoNeg | 21 | 7 | 0 |
| sensitivity stage II CRC/ColoNeg | 27 | 16 | 2 |
| sensitivity stage III CRC/ColoNeg | 37 | 33 | 11 |
| sensitivity stage IV CRC/ColoNeg | 36 | 57 | 57 |

Figure 2:
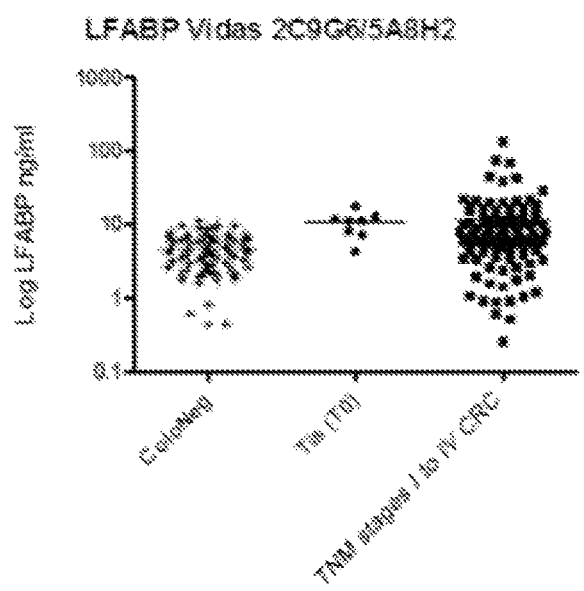
FIG. 2 represents the results of ELISA assay of LFABP on Vidas® in control patients presenting negative coloscopy (ColonNeg), and patients presenting tumors in situ (Tis T0), as described in example 4.

According to FIG. 2, LFABP allows detecting 5 patients out of 8 with a tumor in situ Tis (T0), without detecting negative coloscopy control patient (specificity threshold fixed at 100%, with a detection threshold for LFABP at 11.06 ng/ml). At the same time, we had a good detection of invasive colorectal cancers of stages I to IV by LFABP.

Figure 3:
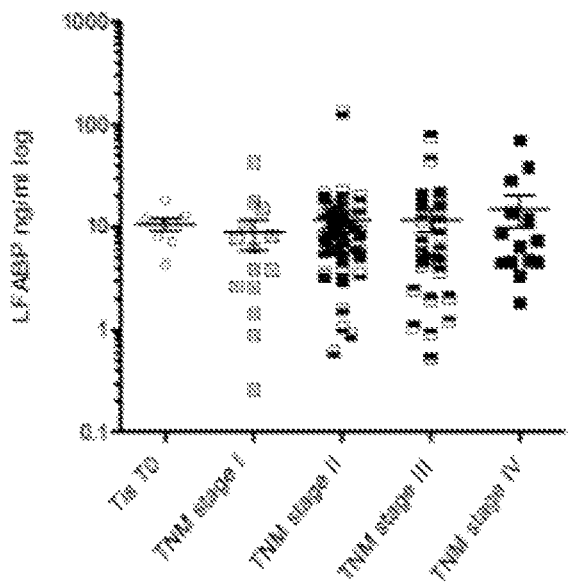

The detection of Tis (T0) compared to negative coloscopies is statistically significant (p=0.0002) with t-test of Mann-Whitney. The same for the detection of invasive colorectal cancers of stages I to IV, illustrated in FIG. 3.

Figure 4:
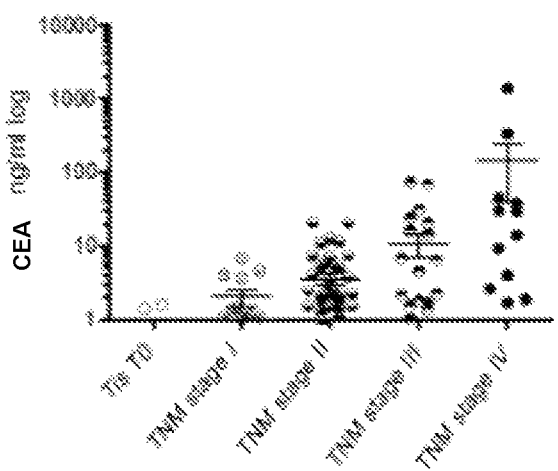
Figure 6:
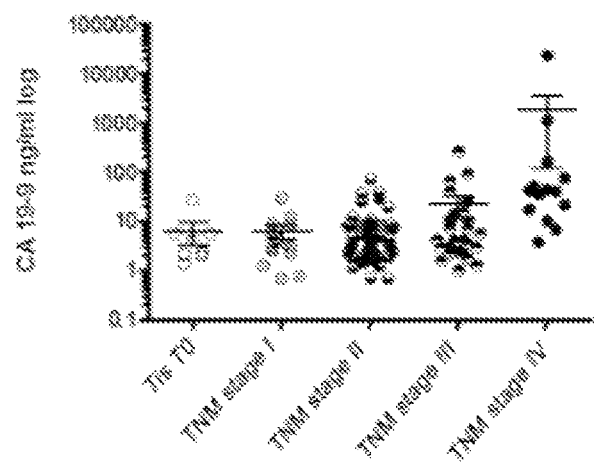

As illustrated in FIGS. 4 and 5, comparatively, with a specificity fixed at 100% for the negative coloscopies control group, no patient has been detected suffering from Tis (T0) with carcinoembryonic antigen marker (CEA). And no patient suffering from adenoma, or patient suffering from Tis (T0), or patient holder of an invasive CRC of TNM stage I with CA19-9 marker, on the tested cohort.

CEA and CA 19-9 marker are tumor markers and they detect advanced stages better than the early stages, the release into the blood of the marker being proportional to the size of the tumor and its aggressiveness.

However, the applicant highlighted, in a surprising way, that LFABP detects both precancerous lesions (adenomas) and tumors in situ that T0 and early stages and advanced stages of invasive colorectal cancer, and therefore allows improving the chances of survival of the patients.

EXAMPLE 5

LFABP Detection by LC-MRM-MS Technique et MRM Cube

1) MRM Technique
1.1) Methodology No Space

The principle of the assays by using Multiple Reaction Monitoring MRM assay technology is based on the association between liquid chromatography and a mass spectrometer of the type hybrid triple quadrupole/ion trap (5500Q trap of AB Sciex) operating in MRM mode (Q1q2Q3). In principle, for each protein of interest, trypsin peptides of interest were chosen. The transitions are predicted for example by means of Midas™ software and pilot MRM™ of AB Sciex.

LFABP marker was quantified via the quantification of one or many for its peptides. These peptides are chosen according to their physicochemical characteristics, and their ability to be detected in the mass spectrometer. The chosen peptides are isolated in the first quadrupole Q1, to be fragmented in the collision cell of the mass spectrometer (q2). From the generated daughter ions, the most representative ions allowing the best specificity were chosen, and the intensity of these daughter ions was monitored after selection in the third quadrupole Q3. The mass couple parent ion/daughter ion is called transition, and it is the association of the transition to the chromatographic retention time corresponding thereto which defines the specificity of the assay with respect to the target protein. To have a quantitative assay, there must be added an internal standard (for example a "heavy" identical peptide that will serve as a standard, in known quantity, which is added to the sample and eluted at the same chromatographic time and which allows relative quantitation). The peptides were selected according to their sensitivity (best response in the mass spectrometer) and to their specificity in the matrix.

Peptides with identical sequences to the selected target peptides were synthesized, with marked lysine or arginine (C13 and N15): +8 Dalton for lysine, +10 Da for arginine, in order to carry out quantitative assays. Indeed, these heavy peptides have the same physicochemical properties as the target peptides, and are eluted at the same chromatographic retention times.

In order to decrease the detection limit to a few ng/ml, an improved MRM-MS method was implemented. The successive steps of this method are: 1) trypsin digestion, 2) SPE fractionation (solid-phase extraction) of peptides, 3) liquid chromatography (LC) coupled with MRM-MS.

The adjustment was carried out on overloaded samples (spike) by adding the synthetic peptides.

Enzymatic Digestion:

Serum samples are denatured in a 6M urea solution buffered with 10 mM Tris pH 8 and containing 30 mM dithiothreitol, for 40 minutes at 40° C., then alkylated with 50 mM iodoacetamide, at room temperature, for 40 minutes, in the dark. They are diluted 6 times in water, then trypsin digestion is carried out at 37° C., over night, by using a ratio enzyme-substrate of 1:30 (Promega). The digestion is stopped by adding formic acid to a final concentration of 0.5%. The digested samples are desalted by extraction on solid phase (SPE, solid-phase extraction) by using reverse phase cartridges Oasis HLB 3 cc (60 mg) (Waters). After sample application, the cartridges are washed with 1 ml of 0.1% formic acid, then elution was carried out by a methanol/water mixture (80/20 v/v) containing 0.1% formic acid. The eluates are dried in vacuum.

SPE Fractionation:

Dry samples were reworked in 1 ml of acetate buffer and loaded onto the mixed cartridges (hydrophobic and cation exchange) Oasis MCX (mixed cation exchange) 60 mg (Waters) previously equilibrated into acetate buffer and methanol. The cartridges are washed with 1 ml of acetate buffer and 1 ml of methanol. The peptides of interest (Table 8) are eluted with 1 ml of a mixture methanol/acetate buffer (50/50 v/v)). Acetate buffer pH is chosen according to the isoelectric point of the peptide of interest. The eluates are dried in vacuum, dissolved in 200 µl of a solution of acetonitrile/water (3/97 v/v) containing 0.1% formic acid. An aliquot of 50 µl was injected into the LC coupled to MS-MS system.

Liquid Chromatographie and Mass Spectrometry:

LC-MS analysis was performed on a high pressure chromatographic system (HPLC) of the type HP 1100 series with binary pump and injector (Agilent Technologies) coupled to a mass spectrometer, AB Sciex 400 QTrap (hybrid triple quadrupole MS–ion trap) (MDS Sciex) for better sensitivity. LC separation was performed on a Symmetry C18 column (Waters), at an elution flow rate of 300 µl/min. (Eluent A=0.1% formic acid in water, eluent B=0.1% formic acid in acetonitrile, linear gradient from 5% B to 50% B in 25 min, then from 50% B to 100% B in 3 min). MS analysis was carried out in positive ionization mode at a voltage of 5500 V applied to the needle, allowing ionization in the source. Instrument control and data acquisition are carried out with the Analyst 1.4.1 software. The flow rates of the nebulization gas (air) and curtain gas (azote) are 30 and 20 psi, respectively. The ion source VTM Turbo is set at 400° C., the auxiliary nitrogen flow at 40 psi. The collision energy (CE), the port voltage (DP, declustering potential) and the voltage at the outlet of the collision cell (CXP, collision cell exit potential) are optimized for each of the selected MRM transitions.

All parent ion di- or tri charged with theoretical trypsin peptides in a mass interval ranging from 800 to 3,000 Da and all possible fragment ions of y or b type. For each protein, each possible transition was tested in order to determine the most sensitive and most specific transitions. The result of this selection is summarized in Table 8. The MCX chromatographic separation was carried out at different pH levels, the pH chosen for the experiments that will follow being the pH which allows to obtain the area of the highest peak.

The list of MRM theoretical transitions of the sequences SEQ ID NO: 5 to 7 for the assay of the LFABP marker were generated by using MIDAS software (MRM-initiated Detection and Sequencing). This list comprises 3 peptides of LFABP protein, and for each peptide, several transitions are followed.

TABLE 8

Peptides and transitions used for the assay of LFABP
LFABP

| Séquences (SEQ ID N°) | pI | TR | Q1 (natural light peptide) | Q3 (natural light peptide) | Q1 (standard internal heavy peptide) | Q3 (standard internal heavy peptide) | DP | EP | CE | CXP |
|---|---|---|---|---|---|---|---|---|---|---|
| AIGLPEELIQK (SEQ ID N° 5) | 4.31 | 16.75 | 605.9 | 630.6 | 609.9 | 638.6 | 120 | 2.2 | 35 | 34.5 |
|  |  |  |  | 759.7 |  | 767.7 | 120 | 2.2 | 34 | 30 |
|  |  |  |  | 856.2 |  | 864.2 | 120 | 2.2 | 20 | 36 |
| GVSEIVQNGK (SEQ ID N° 6) | 6.99 | 9.4 | 515.8 | 545.3 | 519.8 | 553.3 | 108 | 2.2 | 19.8 | 31 |
|  |  |  |  | 874.5 |  | 882.5 | 108 | 2.2 | 23.3 | 31 |
|  |  |  |  | 658.4 |  | 666.4 | 108 | 2.2 | 23.3 | 31 |
| TVVQLEGDNK (SEQ ID N° 7) | 4.11 | 9.65 | 551.8 | 675.3 | 555.8 | 683.3 | 88 | 4.2 | 25.7 | 16 |
|  |  |  |  | 803.4 |  | 811.4 | 88 | 4.2 | 18.9 | 17.5 |
|  |  |  |  | 902.4 |  | 910.4 | 88 | 4.2 | 16 | 21 |

In addition, by using an internal standard, for example a heavy peptide of AQUA (Sigma) type or even a heavy recombinant protein that will serve as assay standard, or any other method of standardization known by the one skilled in the art, it is possible to absolutely quantify the tumor marker of interest in a complex biological medium.

In a preferred mode of the invention, the transitions 605.9/856.5 of the peptide of SEQ ID NO: 5, and its transition to the corresponding heavy peptide will be followed up. The ratio of the areas of the chromatographic peak of the natural transition divided by the area of the heavy transition will be established to obtain one assay per transition for each sample, then the assay obtained for the different transitions will be summarized or not between them, for example by the median polish method according to Tukey procedure.

2) LFABP Detection by MRM Cubed Technique
2.1) Methodology

This is a new method developed by the authors of the invention, which allows increasing signal/noise ratio and the analytic specificity of an assay. In a complex fluid as serum, the increase of analytic specificity allows an increase of the observed sensitivity. This method has a longer time of adjustment, and it also implies a longer acquisition time for each sample.

With this method, LFABP was quantified, via peptide of SEQ ID NO: 5.

The method is developed on a mass spectrometer of the type hybrid triple quadrupole/ion trap (5500Q trap of AB Sciex) and consists in i) selection of peptidic proteotypic ion in Q1, ii) CID activation of the selected ion in Q2, ii) capture of one of the most intense fragment ions in Q3, which defines the optimal MRM transition, iv) activation of this daughter ion to generate fragments of second generation, v) selective scan of the masses generated from these second generation ions. After acquisition, an MRM3 chromatogram is reconstructed after extraction of one or many ions produced from second generation for quantification.

This very specific methodology allows limiting the sample pre-treatment. In this example, the only sample pretreatment was an extraction of peptides in solid phase on a cation exchange column. The platform uses conventional chromatographic columns of 2.1 mm.

2.2) Correlation Between the Different Methods of Assay

To ensure the robustness of our assay methods, and of the clinical validity of the LFABP marker, we examined:

- Coefficients of variation of the assays, their repeatability and reproducibility
- Consistency of the assays by repeating the same assays on several samples several months apart: the connection coefficient for Vidas® assays of LFABP was 99%, the correlation of connection for LFABP MRM test (of SEQ ID NO: 5, 605.9/856.5) 98%.
- The correlation between the different assays. The measure of the correlation was carried out by both a linear regression test and a Spearman correlation test.

A good correlation is observed between two peptides of LFABP protein, carried out by a test on 182 patients: of SEQ ID NO: 7 and SEQ ID NO: 5. These two independent MRM assays are therefore assaying properly the same molecule. A good correlation between the MRM assay of the peptide of SEQ ID NO: 5 and the 2C9G6/5A8H2 ELISA assay, was observed.

As shown in Table 9 below, the correlation between the ELISA Vidas® tests and MRM and MRM3 tests is good ($r^2$ greater than 0.90 in all cases).

TABLE 9

Correlation between the different methods of assay evaluated on 8 Tis, 104 invasive CRC, 70 blood donor patients and 31 ColoNeg

|  | MRM SEQ ID NO: 5 856.5 | MRM3 | Vidas® 2C9G6/ 5A8H2 | Vidas® 5A8H2/ 3D6G1 | ELISA Hycult biotech |
|---|---|---|---|---|---|
| MRM of SEQ ID N° 5 605.9/856.5 | 1 | 0.94 | 0.9 | 0.92 | 0.8 |
| MRM3 | 0.94 | 1 | 0.9 | 0.9 | 0.77 |
| VIDAS® | 0.9 | 0.9 | 1 | 0.96 | 0.73 |

TABLE 9-continued

Correlation between the different methods of assay evaluated on 8 Tis, 104 invasive CRC, 70 blood donor patients and 31 ColoNeg

| | MRM SEQ ID NO: 5 856.5 | MRM3 | Vidas® 2C9G6/ 5A8H2 | Vidas® 5A8H2/ 3D6G1 | ELISA Hycult biotech |
|---|---|---|---|---|---|
| 2C9G6/5A8H2 Vidas® 5A8H2/3D6G1 | 0.92 | 0.9 | 0.96 | 1 | 0.81 |
| Commercial ELISA | 0.8 | 0.77 | 0.73 | 0.81 | 1 |

The invention claimed is:

1. A method of detecting and treating non-cancerous colorectal lesions likely to evolve into invasive colorectal cancer (CRC) in a patient, the method comprising:
   obtaining a biological sample from the patient, said sample being distant from the colorectal lesion;
   detecting the quantity of the peptide comprising SEQ ID NO: 1 present in the sample;
   comparing the quantity of said peptide in the sample against a quantity of said peptide in a reference population;
   diagnosing the patient as having a non-cancerous colorectal lesion likely to evolve into an invasive colorectal cancer when the quantity of said peptide in the sample is increased compared to the quantity of said peptide in the reference population; and
   treating the patient by exeresis of the non-cancerous colorectal lesion.

2. The method according to claim 1, wherein the biological sample of the patient is whole blood, serum, plasma, urine, cerebrospinal fluid, organic secretions, saliva, effusions, feces, bone marrow, cells purified from these samples, a tissue, or isolated cells.

3. The method according to claim 2, wherein the biological sample is whole blood, serum, or plasma.

4. The method according to claim 1, wherein the peptide is detected by a mass spectrometry technique.

5. The method according to claim 4, wherein the peptide is detected by LC-MRM-MS technique which combines liquid chromatography and mass spectrometry in MRM mode (Multiple Reaction Monitoring).

6. The method according to claim 4, wherein the mass spectrometry technique further detects at least one peptide comprising SEQ ID NO: 2, SEQ ID NO: 3, SEQ ID NO: 4, SEQ ID NO: 5, SEQ ID NO: 6, or SEQ ID NO: 7.

7. The method according to claim 1, wherein the peptide is detected using an ELISA technique.

8. The method according to claim 1, wherein the peptide is detected by an enzymatic technique.

9. The method according to claim 1, wherein the reference population is a population of non-suspected CRC patients.

* * * * *